US011827622B2

(12) United States Patent
Zhu et al.

(10) Patent No.: US 11,827,622 B2
(45) Date of Patent: Nov. 28, 2023

(54) CRYSTALLINE FORMS OF IMIDACLOPRID AND METHODS OF USE THEREOF

(71) Applicant: New York University, New York, NY (US)

(72) Inventors: Xiaolong Zhu, New York, NY (US); Jingxiang Yang, New York, NY (US); Chunhua T. Hu, New York, NY (US); Michael D. Ward, New York, NY (US); Bart Kahr, Brooklyn, NY (US)

(73) Assignee: NEW YORK UNIVERSITY, NY, NY (US)

( * ) Notice: Subject to any disclaimer, the term of this patent is extended or adjusted under 35 U.S.C. 154(b) by 0 days.

(21) Appl. No.: 17/547,456

(22) Filed: Dec. 10, 2021

(65) Prior Publication Data

US 2022/0204480 A1     Jun. 30, 2022

Related U.S. Application Data

(60) Provisional application No. 63/124,500, filed on Dec. 11, 2020.

(51) Int. Cl.
*C07D 403/06*     (2006.01)
*A01N 43/50*     (2006.01)

(52) U.S. Cl.
CPC ........... *C07D 403/06* (2013.01); *A01N 43/50* (2013.01); *C07B 2200/13* (2013.01)

(58) Field of Classification Search
CPC .................................................. C07D 403/06
See application file for complete search history.

(56) References Cited

PUBLICATIONS

Zhu, J. Am. Chem. Soc. 2021, 143, 17144-17152.*
Lee FAng, The Intercept, Jan. 18, 2020.*
Klingelhofer, Environmental Research 213 (2022) 113727.*
Stephens, P. J. Devlin, F. J. Chabalowski, C. F. & Frisch, M. J. Ab initio calculation of vibrational absorption and circular dichroism spectra using density functional force fields. 98, 11623-11627 (1994).
Dhananjay, D. Chetan, S. S. Kaushik, B. Deepak, C. CCDC 943833: Experimental Crystal Structure Determination, DOI: 10.5517/cc10p472 (2015).
United Nations sustainable development goals. https://sustainabledevelopment.un.org/topics/sustainabledevelopmentgoals.
McBeath, J. A brief history and future potential of neonicotinoid use in public health. Int. Pest Control 59, 214-215 (2017).
Oxborough, R. M. et al. Susceptibility testing of Anopheles malaria vector with the neonicotinoid insecticide, clothianidin; results from 16 African countries, in preparation for indoor residual spraying with new insecticide formulations, Malaria J. 18, 264 (2019).
Kupferschmidt, K. Pick your poison. Science 354, 171-173 (2016).
Georghiou, G. P. & Mellon, R. B. Pesticide resistance in time and space. In Pest Resistance to Pesticides, 1-46 (Springer, Boston, 1983).
World Health Organization. Prequalified lists: vector control products. (WHO, Geneva, 2020).
World Health Organization. A Global Brief on Vector-Borne Diseases (WHO, Geneva, 2014).
WHO Prequalification Team. Cielo ULV adulticide space spray. (WHO, Geneva, 2019).
Pridgeon, J. W. et al. Susceptibility of Aedes aegypti, Culex quinquefasciatus Say, and Anopheles quadrimaculatus to 19 pesticides with different modes of action. J Med Entomol 45, 82-87 (2008).
Yamamoto, I. & Casida, J. E. Nicotinoid Insecticides and the Nicotinic Acetylcholine Receptor (Springer-Verlag, Tokyo, 1999).
Sheets, L. P. Imidacloprid a neonicotinoid insecticide. In Hayes' Handbook of Pesticide Toxicology, 3rd ed., ch 95, 2055-2064 (Elsevier Academic Press, San Diego, 2010).
Simon-Delso, N. et al. Systemic insecticides (neonicotinoids and fipronil): trends, uses, mode of action and metabolites. Environ. Sci. Pollut. Res. 22, 5-34 (2015).
Buchholz, A. & Nauen, R. Translocation and translaminar bioavailability of two neonicotinoid insecticides after foliar application. Pest Manage. Sci. 58, 10-16 (2002).
Weichel, L. & Nauen, R. Uptake, translocation and bioavailability of imidacloprid in several hop varieties. Pest Manag. Sci. 60, 440-446 (2003).
Goulson, D. Review: an overview of the environmental risks posed by neonicotinoid insecticides. J. Appl. Ecol. 50, 977-987 (2013).
Morrissey, C. A. et al. Neonicotinoid contamination of global surface waters and associated risk to aquatic invertebrates: a review. Environ. Int. 74, 291-303 (2015).
Hallmann, C. A. Foppen, R. P. B. van Turnhout, C. A. M. de Kroon, H. & Jongejans, E. Declines in insectivorous birds are associated with high neonicotinoid concentrations. Nature 511, 341-343 (2014).
Eng, M. Stutchbury, B. Morrissey, C. A neonicotinoid insecticide reduces fueling and delays migration in songbirds. Science 365, 1177-1180 (2019).
van Klink, R. et al. Meta-analysis reveals declines in terrestrial but increases in freshwater insect abundances. Science 368, 417-420 (2020).
Basset, Y. & Lamarre, G. P. Toward a world that values insects. Science 364, 1230-1231 (2019).
Whitehorn, P. R. O'Connor, S. Wackers, F. L. & Goulson, D. Neonicotinoid pesticide reduces bumble bee colony growth and queen production. Science 336, 351-352 (2012).
Kessler, S. C. et al. Bees prefer foods containing neonicotinoid pesticides. Nature, 521, 74-76 (2015).
Stanley, D. A. et al. Neonicotinoid pesticide exposure impairs crop pollination services provided by bumblebees. Nature 528, 548-550 (2015).
Crall, J. D. et al. Neonicotinoid exposure disrupts bumblebee nest behavior, social networks, and thermoregulation. Science 362, 683-686 (2018).

(Continued)

*Primary Examiner* — Nizal S Chandrakumar
(74) *Attorney, Agent, or Firm* — Troutman Pepper Hamilton Sanders LLP

(57) ABSTRACT

The present invention relates to crystalline polymorphs of imidacloprid for effective pest management strategies at lower dosages. The present invention further relates to processes of preparing the crystalline polymorphs, and to methods of controlling pests using the novel crystalline polymorphs.

14 Claims, 31 Drawing Sheets

(56) References Cited

PUBLICATIONS

Sánchez-Bayo, F., Goulson, D., Pennacchio, F., Nazzi, F., Goka, K., Desneux, N. Are bee diseases linked to pesticideinsecticides?—a brief review. Environ. Int. 89, 7-11 (2016).

Biodiversity Act, 2016. Law No. 2016-1087, Aug. 8, 2016, For the return of biodiversity, nature, and countryside. https://www.legifrance.gouv.fr/eli/loi/2016/8/8/2016-1087/jo/texte.

Pretty, J. & Bharucha, Z. P. Integrated Pest Management for sustainable intensification of agriculture in Asia and Africa. Insects 6, 152-182 (2015).

Dzul-Manzanilla, F. et al. Field efficacy trials of aerial ultra-low-volume application of insecticides against caged Aedes aegypti in Mexico. J. Am. Mosquito. Contr. 35, 140-146 (2019).

Yang, J. et al. DDT polymorphism and the lethality of crystal forms. Angew. Chem. Int. Ed. 56, 10165-10169 (2017).

Yang, J. et al. Inverse correlation between lethality and thermodynamic stability of contact insecticide polymorphs. Cryst. Growth Des. 19, 1839-1844 (2019).

Zhu, X. et al. Manipulating solid forms of contact insecticides for infectious disease prevention. J. Am. Chem. Soc. 141, 16858-16864 (2019).

Yang, J. et al. A deltamethrin crystal polymorph for more effective malaria control. Proc. Natl. Acad. Sci. U.S.A. 117, 26633-26638 (2020).

Zhao, J. Wang, M. Dong, B. Feng, Q. & Xu, C. Monitoring the polymorphic transformation of imidacloprid using in situ FBRM and PVM. Org. Proc. Res. Dev. 17, 375-381 (2013).

Kagabu, S. & Matsuno, H. Chloronicotinyl insecticides. 8. Crystal and molecular structures of imidacloprid and analogous compounds. J. Agric. Food Chem. 45, 276-281 (1997).

Chopra, D. Mohan, T. P. Rao, K. S. & Row, T. N. G. (2E)-1-[(6-Chloropyridin-3-yl)methyl]-N-nitro- imidazolidin-2-imine (imidachloprid). Acta Crystallogr. Sect. E: Struct. Rep. Online 60, 02415-02417 (2004).

Zhu, Q. et al. Resorcinol crystallization from the melt: A new ambient phase, and new "riddles". J. Am. Chem. Soc. 138, 4881-4889 (2016).

Shtukenberg, A. G. et al. Powder diffraction and crystal structure prediction reveal four new coumarin polymorphs. Chem. Sci. 8, 4926-4940 (2017).

Shtukenberg, A. G. Punin, Y. O. Gunn, E. & Kahr, B. Spherulites, Chem. Rev. 112, 1805-1838 (2012).

Shtukenberg, A. G. Zhu, X. Yang, Y. Kahr, B. Common occurrence of twisted molecular crystal morphologies from the melt. Cryst. Growth Des. 20, 6186-6197 (2020).

Mitchell, C. A. Yu, L. & Ward, M. D. Selective nucleation and discovery of organic polymorphs through epitaxy with single crystal substrates. J. Am. Chem. Soc. 123, 10830-10839 (2001).

Yu, L. Nucleation of one polymorph by another. J. Am. Chem. Soc. 125, 6380-6381 (2003).

Jiang, Q. Ward, M. D. Crystallization under nanoscale confinement. Chem. Soc. Rev. 43, 2066-2079 (2014).

Schneider, D. Using Drosophila as a model Insect. Nat. Rev. Genet. 1, 218-226 (2000).

Lozano-Fuentes, S. Saavedra-Rodriguez, K. Black, W. C. & Eisen, L. QCal: A software application for the calculation of dose-response curves in insecticide resistance bioassays. J. Am. Mosq. Control. Assoc. 28, 59-61 (2012).

Grubaugh, N. D. et al. Genomic epidemiology reveals multiple introductions of Zika virus into the United States. Nature 546, 401-405 (2017).

Metsky, H. C. et al. Zika virus evolution and spread in the Americas. Nature 546, 411-415 (2017).

Barrett, A. D. T. The reemergence of yellow fever. Science 361, 847-848 (2018).

Smol, J. P. Climate change: a planet in flux. Nature 483, S12-S15 (2012).

Riaz, M. A. et al. Molecular mechanisms associated with increased tolerance to the neonicotinoid insecticide imidacloprid in the dengue vector Aedes aegypti. Aquat. Toxicol. 126, 326-337 (2013).

Frisch, G. et al. Gaussian 16, Revision A. 03. (Gaussian, Inc., Wallingford, 2016).

\* cited by examiner

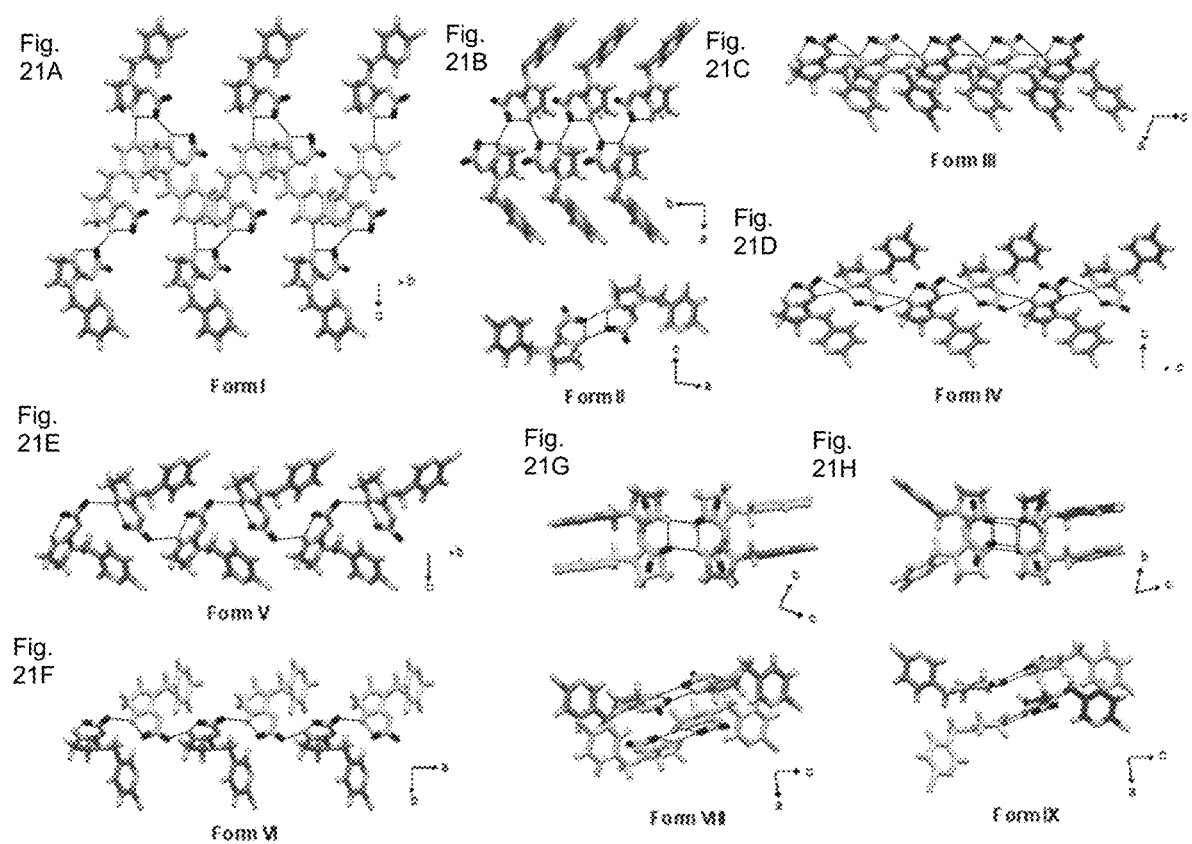

Form III

Form IV

Form V

Form IX nano-VII

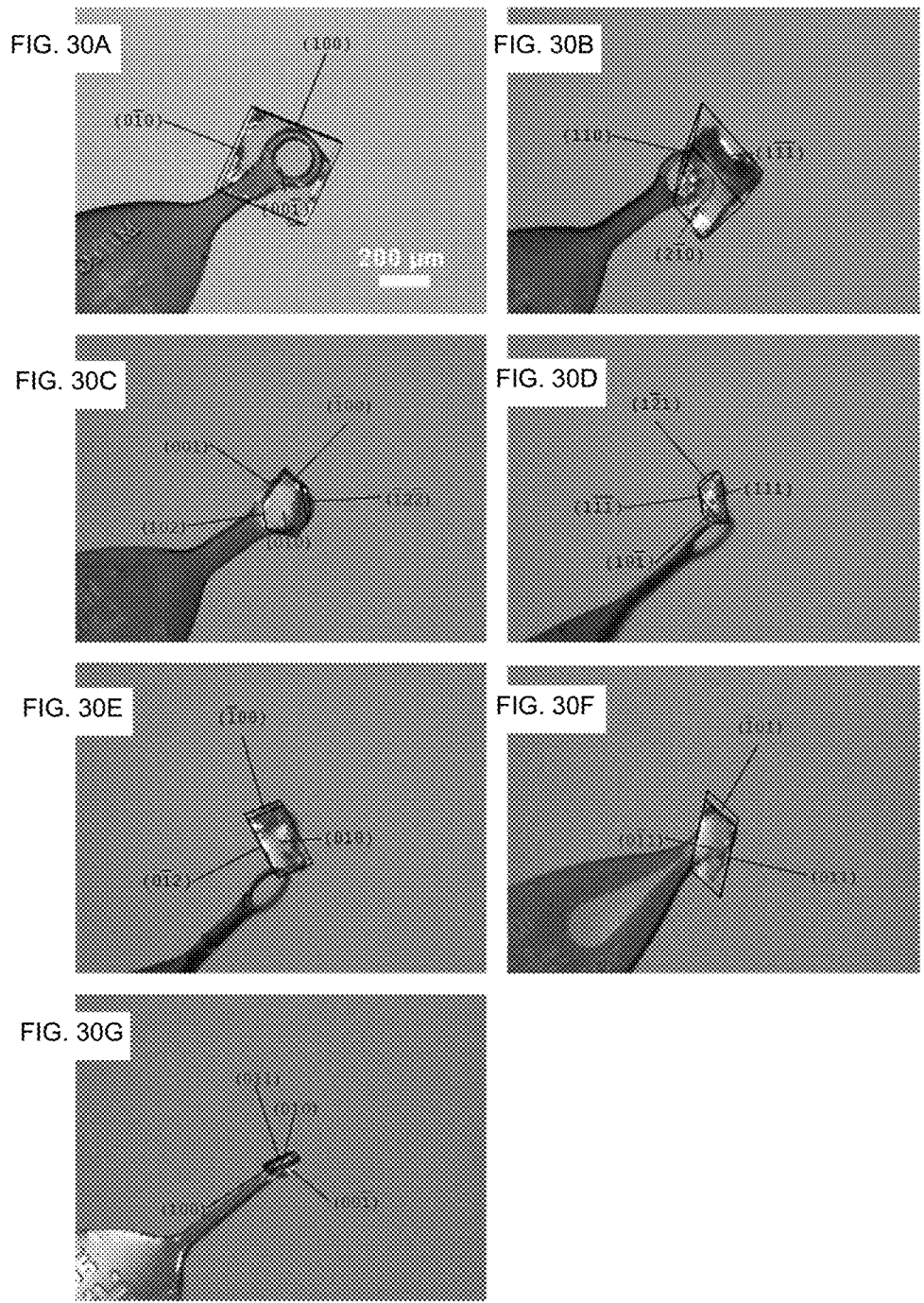

CRYSTALLINE FORMS OF IMIDACLOPRID AND METHODS OF USE THEREOF

CROSS-REFERENCE TO RELATED APPLICATIONS

This application claims priority to U.S. Provisional Patent Application No. 63/124,500, filed on Dec. 11, 2020, the disclosure of which is herein incorporated by reference in its entirety.

STATEMENT AS TO FEDERALLY FUNDED RESEARCH

This invention was made with United States Government support under grant DMR1420073 awarded by National Science Foundation. The Government has certain rights to this invention.

FIELD OF INVENTION

The present invention relates to methods for selectively producing crystalline forms of a neonicotinoid compound imidacloprid, which are useful as pest control agents and disease vector control agents.

BACKGROUND OF THE INVENTION

Polymorphism is the ability for a compound to recrystallize in one or more different forms, each polymorph or form can have different physical properties. As such, compounds with one or more forms may result in improved properties for various applications. In particular, imidacloprid (IMI, 1-[(6-chloro-3-pyridinyl)-methyl]-N-nitro-2-imidazolidinimine), which is represented by Formula 1A below, in imidacloprid crystalline Form I, is the world's leading insecticide and has been approved recently for controlling infectious disease vectors.

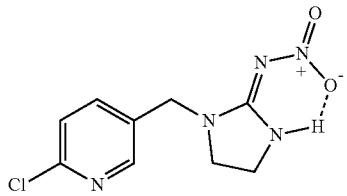

(Formula 1A)

IMI Form I is now used in indoor and outdoor space sprays to control the *Aedes* mosquito, a vector for dengue, chikungunya, yellow fever, and Zika virus. IMI also has the potential to control *Anopheles* and *Culex* mosquitoes, vectors for malaria and lymphatic filariasis, respectively. In space spray applications, IMI functions as a contact insecticide wherein insects absorb the toxicant molecules through the direct contact of tarsi with the surfaces of IMI microcrystals.

High insecticidal potency and low mammalian toxicity have ensured the popularity of IMI (the world's leading insecticide); however, the extensive use of IMI in agriculture appears to be connected to a decrease in insect biomass and especially worrying declines in bee colonies, known as colony collapse disorder (CCD).

Thus, there is a strong unmet need for strategies that enhance IMI contact activity so as to reduce the amount used with concomitant reductions in its exposure to non-target organisms.

SUMMARY OF THE INVENTION

The present disclosure relates to novel crystal forms of imidacloprid and methods for making the same. An exemplary embodiment of the present disclosure provides a crystalline form of imidacloprid, which is Form IX.

In one embodiment, the present disclosure provides a crystalline form of imidacloprid which is Form IX having a Raman spectrum substantially as shown in FIG. 2.

In another embodiment, the present disclosure provides a crystalline form of imidacloprid which is Form IX having an X-ray diffraction pattern substantially as shown in FIG. 12.

In another embodiment, the present disclosure provides a crystalline form of imidacloprid which is Form IX having an X-ray diffraction pattern comprising peaks at 10.2, 11.2, 16.7, 18.0, 21.2, 23.0, 25.2, 26.0, 27.6, 29.1, and 30.2 degrees two-theta (2θ) [CuKa radiation, λ=1.54178 Å.

In another embodiment of the present disclosure provides a crystalline form of imidacloprid, which is Form VIII.

In one embodiment, the present disclosure provides a crystalline form of imidacloprid which is Form VIII having a Raman spectrum substantially as shown in FIG. 3.

In another embodiment, the present disclosure provides a crystalline form of imidacloprid which is Form VIII having an X-ray diffraction pattern substantially as shown in FIG. 13.

In another embodiment, the present disclosure provides a crystalline form of imidacloprid which is Form VIII having an X-ray diffraction pattern comprising peaks at 9.5, 11.2, 16.5, 18.8, 20.8, 22.6, 25.7, 27.8, 28.7, and 30.2 degrees two-theta (2θ).

In another embodiment of the present disclosure provides a crystalline form of imidacloprid, which is Form VII.

In one embodiment, the present disclosure provides a crystalline form of imidacloprid which is Form VII having a Raman spectrum substantially as shown in FIG. 4.

In another embodiment, the present disclosure provides a crystalline form of imidacloprid which is Form VII having an X-ray diffraction pattern substantially as shown in FIG. 14.

In another embodiment, the present disclosure provides a crystalline form of imidacloprid which is Form VII having an X-ray diffraction pattern comprising peaks at 12.9, 17.0, 19.3, 20.0, 23.6, 25.4, 30.4, and 32.2 degrees two-theta (2θ).

In another embodiment of the present disclosure provides a crystalline form of imidacloprid, which is Form VI.

In one embodiment, the present disclosure provides a crystalline form of imidacloprid which is Form VI having a Raman spectrum substantially as shown in FIG. 5.

In another embodiment, the present disclosure provides a crystalline form of imidacloprid which is Form VI having an X-ray diffraction pattern substantially as shown in FIG. 15.

In another embodiment, the present disclosure provides a crystalline form of imidacloprid which is Form VI having an X-ray diffraction pattern comprising peaks at 11.2, 11.9, 12.9, 15.8, 17.4, 18.5, 20.0, 21.3, 22.6, 26.3, 28.7, and 30.7 degrees two-theta (2θ).

In another embodiment of the present disclosure provides a crystalline form of imidacloprid, which is Form V.

In one embodiment, the present disclosure provides a crystalline form of imidacloprid which is Form V having a Raman spectrum substantially as shown in FIG. 6.

In another embodiment, the present disclosure provides a crystalline form of imidacloprid which is Form V having an X-ray diffraction pattern substantially as shown in FIG. 16.

In another embodiment, the present disclosure provides a crystalline form of imidacloprid which is Form V having an X-ray diffraction pattern comprising peaks at 8.8, 12.5, 14.3, 15.6, 17.6, 19.7, 21.0, 21.7, 24.1, 28.7, and 30.6 degrees two-theta (2θ).

In another embodiment of the present disclosure provides a crystalline form of imidacloprid, which is Form IV.

In one embodiment, the present disclosure provides a crystalline form of imidacloprid which is Form IV having a Raman spectrum substantially as shown in FIG. 7.

In another embodiment, the present disclosure provides a crystalline form of imidacloprid which is Form IV having an X-ray diffraction pattern substantially as shown in FIG. 17.

In another embodiment, the present disclosure provides a crystalline form of imidacloprid which is Form IV having an X-ray diffraction pattern comprising peaks at 8.2, 11.8, 15.2, 16.5, 19.0, 21.7, 22.8, 25.3, 27.7, and 30.0 degrees two-theta (2θ).

In another embodiment of the present disclosure provides a crystalline form of imidacloprid, which is Form III.

In one embodiment, the present disclosure provides a crystalline form of imidacloprid which is Form III having a Raman spectrum substantially as shown in FIG. 8.

In another embodiment, the present disclosure provides a crystalline form of imidacloprid which is Form III having an X-ray diffraction pattern substantially as shown in FIG. 18.

In another embodiment, the present disclosure provides a crystalline form of imidacloprid which is Form III having an X-ray diffraction pattern comprising peaks at 8.3, 11.9, 13.2, 20.3, 22.1, 23.3, 23.9, 24.7, 26.7, 28.2, and 30.7 degrees two-theta (2θ).

Some embodiments of the present disclosure provide a process for preparing the crystalline imidacloprid. The present disclosure provides a process for preparing the crystalline Form IX comprising melting imidacloprid Form I at about 180° C., cooling imidacloprid Form I to approximately 80° C. in an ambient environment with a temperature of approximately 25° C., and growing crystals of imidacloprid Form IX from the molten imidacloprid.

In another embodiment, the present disclosure provides a process for preparing the crystalline Form VIII comprising melting imidacloprid Form I at about 180° C., cooling imidacloprid Form I at a temperature of about 25° C. to about 85° C., and growing crystals of imidacloprid Form VIII from the molten imidacloprid.

In another embodiment, the present disclosure provides a process for preparing the crystalline Form VII comprising melting imidacloprid Form I at about 180° C., diffusing the molten imidacloprid into a porous medium, cooling imidacloprid Form I to about 25° C., and growing crystals of imidacloprid Form VII within the porous media.

In another embodiment, the present disclosure provides a process for preparing the crystalline Form VII further comprising seeding the molten imidacloprid with Form VII crystals and growing crystals of imidacloprid Form VII.

In another embodiment, the present disclosure provides a process for preparing the crystalline Form VI further comprising seeding the molten imidacloprid with Form III crystals and growing crystals of imidacloprid Form VI.

In another embodiment, the process for preparing the crystalline Form V can further comprise a step of phase transforming Form IX into crystalline Form V.

In another embodiment, the present disclosure provides a process for preparing the crystalline Form IV comprising combining imidacloprid Form I with ethanol, forming an imidacloprid-saturated ethanol solution, evaporating the ethanol, and growing crystals of imidacloprid Form IV from the imidacloprid-saturated ethanol solution.

In one embodiment, the present disclosure provides a process for preparing the crystalline Form III comprising phase transforming Form IX into crystalline Form III.

In another embodiment, the present disclosure provides a process for preparing the crystalline Form III comprising melting imidacloprid Form I at about 180° C., cooling imidacloprid Form I at a temperature of about 25° C. to about 80° C., growing crystals of imidacloprid Form IX from the molten imidacloprid, phase transforming imidacloprid Form IX into crystalline Form VI, seeding the molten imidacloprid with Form VI crystals and growing crystals of imidacloprid Form III.

In any one of the embodiments, the present disclosure provides the crystalline form is substantially isolated.

In any one of the embodiments, the present disclosure provides the crystalline form is substantially free of other crystalline forms.

In another aspect, the present disclosure provides a pesticidal composition comprising any crystalline form disclosed herein.

In another embodiment, the pesticidal composition comprises the crystalline form in the composition in an amount of about 0.5% to about 75% by weight.

In one embodiment, the present disclosure provides a method of controlling a pest comprising applying to the pest or its locus the crystalline form of any the crystalline forms as described above or the pesticidal composition as described above.

In one embodiment, the pest is an insect.

In one embodiment, the pest is a disease vector.

In one embodiment, the disease is selected from Zika virus, yellow fever, dengue fever, chikungunya virus, lyme disease, plague, malaria, leishmaniasis, filariasis, sleeping sickness, West Nile fever, Japanese encephalitis, Rift Valley fever, and combinations thereof.

In one embodiment, the insect is selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas (indoors & outdoors), flea beetles, flies, flesh flies, fruit flies, fungus gnats (sciarid flies), gnats, grasshoppers, green bottle flies, green-striped mapleworms, ground beetles, grubs, gypsy moths (larvae), hide beetles, house flies, hornets, horseflies, houseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, medflies, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, red-humped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellow-necked caterpillar, wasps, and webworms.

In one embodiment, the insect is a mosquito.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 21A-22H depict crystal structures of imidacloprid Forms I, II, III, IV, V, VI, VIII, and IX with hydrogen bonds represented in dashed lines.

FIG. 27A shows onset temperature and peak temperature of melting of imidacloprid Form I. FIG. 27B shows heating of imidacloprid Form I melt on DSC, which was prepared by quenching from 180° C. to −60° C. at 50° C./min.

FIGS. 29A and 28B show the preparation of imidacloprid Forms III and VI by seeding nucleation.

FIGS. 30A-30G show single crystals of imidacloprid Forms I, III, IV, V, VI, VIII, and IX with Miller indices.

FIG. 32A shows transformation of Form IX to Form V at 95° C. which was followed by the melting of Form IX and the transformation of Form V to Form I at 110° C. FIG. 32B shows transformation of Form IX to Forms V and VI, and finally to Form I at 80° C. FIG. 32C shows transformation of Form IX to Form I at 100° C.

DETAILED DESCRIPTION

Figure 1:
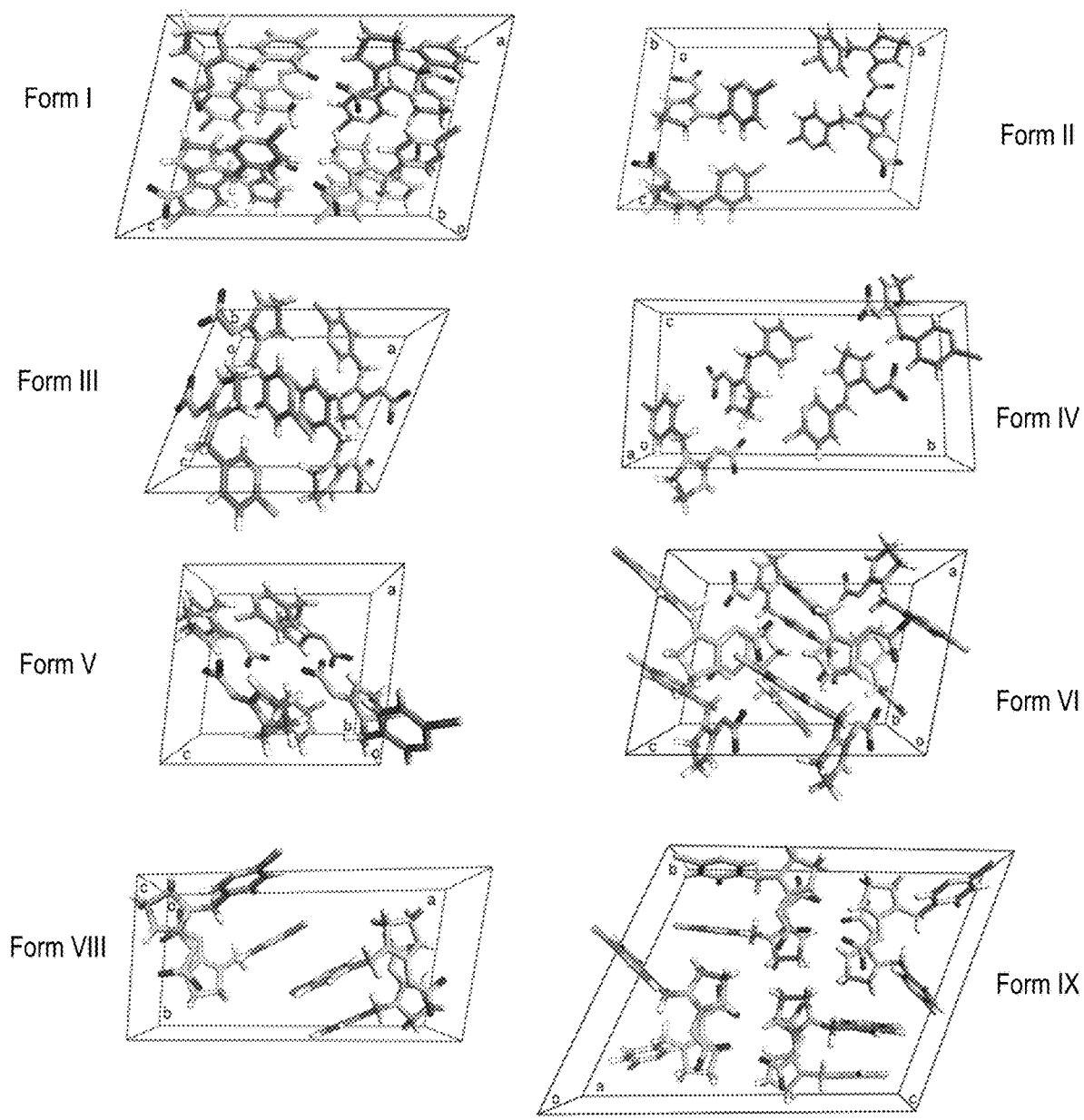
FIG. 1 depicts the crystal packing diagrams in unit cells of imidacloprid Forms I, II, III, IV, V, VI, VIII, and IX.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

A "pest", as used herein, refers to not only insects, but also is a generic term for small animals that may directly or indirectly damage, and thereby affect, humans, produce, machines, equipment, and so on, by colonizing, attacking, irritating, or feeding upon them, or competing for host nutrients. Examples of pests include mosquitos, flies, ants, spiders, centipedes, cockroaches, geckos, mice, pigeons, crows, and any other similar animals.

As used herein the term "to control a pest" means to expel, kill, destroy, or exterminate pests, prevent or mitigate proliferation of pests, protect targets from pests, and control (or inhibit) the growth of pests. Controlling pests includes enticing pests in order to exert the pest control effects described above.

As used herein the term "pesticidal composition" refers to a composition comprising a substance or mixture of substances capable of expelling, killing, destroying, exterminating, preventing, or mitigating any pest.

As used herein the term "effective" applied to dose or amount refers to that quantity of a pesticide that is sufficient to result in a desired pesticidal action or activity.

Typically, different crystalline forms of the same substance have different bulk properties relating to, for example, hygroscopicity, solubility, stability, and the like. Forms with high melting points often have good thermodynamic stability which is advantageous in prolonging shelf-life of formulations containing the solid form. Forms with lower melting points often are less thermodynamically stable, but are advantageous in that they have increased water solubility, translating to increased drug bioavailability. Forms that are weakly or non-hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms (polymorphs) of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder or thin film diffraction (XRD). Other characterization methods such as Raman spectroscopy, differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms are most commonly characterized by XRD. An XRD pattern of reflections (peaks) is typically considered a fingerprint of a particular crystalline form. It is well known that the relative intensities of the XRD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRD herein is meant to encompass the above-mentioned variations.

In the same way, temperature readings in connection with melting point, DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. One of skill in the art would appreciate that certain analytical techniques, such as, for example, powder XRD, Raman spectroscopy, 1H-NMR, TGA and DSC, will not produce exactly the same results every time due to, for example, instrumental variation, sample preparation, scientific error, etc. Accordingly, a crystalline form reported herein having a DSC thermogram "substantially" as shown in any of the Figures is understood to accommodate such variation.

Further, it should be noted that varying degrees of crystallinity of a cocrystal of a compound, such as the novel cocrystals disclosed herein, may be achieved. The degree of crystallinity achieved may, for example, depend on the conditions under which a sample is prepared. Accordingly, one of skill in the art will appreciate that a particular set of analytical data may reflect a greater or lesser degree of crystallinity than the exemplary analytical data shown in the Figures herein, but appreciate that the form of the compound is, indeed, the same as that disclosed and claimed herein.

As used herein, the terms "imidacloprid," "IMI," and "imidacloprid Forms I, II, III, IV, V, VI, VII, VIII, and XI," and variations thereof, including variations with use the chemical name "1-[(6-chloro-3-pyridinyl)-methyl]-N-nitro-2-imidazolidinimine" in place of the common name "imidacloprid," are used interchangeably to refer to the novel imidacloprid polymorphs described herein.

When a compound recrystallizes from a solution, slurry, within a porous media, or other means, the compound may crystallize with different spatial lattice arrangements, a property referred to as "polymorphism." The different crystal forms are individually referred to as a "polymorph" or "form." Different polymorphic forms of a compound may differ from each other with respect to one or more physical property, such as solubility, true density, crystal shape, compaction behavior, flow properties, lethality, solid state stability, and the like.

As shown in FIGS. 1 and 30, eight of the nine IMI polymorphs were attainable as single crystals that were amenable to single-crystal X-ray diffraction at 100K.

The crystal structure of imidacloprid Form IX has been determined under single-crystal X-ray diffraction at 100 K (space group no. P-1(2), Z=8, a=6.4692(4) Å, b=17.2049(10) Å, c=21.3255(12) Å, V=2156.8(2) Å$^3$).

The crystal structure of imidacloprid Form VIII has been determined under single-crystal X-ray diffraction at 100 K (space group no. P-1(2), Z=4, a=6.4420(4) Å, b=9.2449(5) Å, c=18.5409(11) Å, V=1075.80(11) Å$^3$).

The crystal structure of imidacloprid Form VI has been determined under single-crystal X-ray diffraction at 100 K (space group no. P2$_{1/c}$ (14), Z=8, a=10.7171(12) Å, b=13.8254(16) Å, c=15.2387(17) Å, V=2214.8(4) Å$^3$).

The crystal structure of imidacloprid Form V has been determined under single-crystal X-ray diffraction at 100 K (space group no. P2$_{1/c}$ (14), Z=4, a=10.050(3) Å, b=9.961(3) Å, c=10.830(4) Å, V=1076.4(6) Å$^3$).

The crystal structure of imidacloprid Form IV has been determined under single-crystal X-ray diffraction at 100 K (space group no. P2$_{1/c}$ (14), Z=4, a=4.8498(5) Å, b=21.120(2) Å, c=10.5617(10) Å, V=1070.72(18) Å$^3$).

TABLE 1

| Form | Raman Shift (cm$^{-1}$) |
|---|---|
| I | 3374.8, 1189.8, 1109.6, 1196.4, 321.1, 282.0, 244.0, 198.8 |
| II | 3345.5, 1104.8, 322.6, 310.6, 252.0 |
| III | 3350.5, 1192.8, 1101.9, 329.2, 284.1, 246.0 |
| IV | 3413.6, 1104.1, 329.3, 293.4 |
| V | 3415.8, 1133.2, 1104.1, 326.6, 308.8, 270.8, 250.3 |
| VI | 3413.9, 3381.3, 1106.7, 1101.6, 309.3, 267.6, 250.4 |
| VII | 3347.4, 1107.0, 323.0, 312.1, 253.4 |
| VIII | 3469.1, 1188.7, 1101.1, 310.2, 283.8 |
| IX | 3447.0, 1188.2, 1104.2, 312.1, 282.4, 251.0 |

Polymorphs I, II, III, IV, VI, VII, VIII, and XI of imidacloprid exhibit an X-ray diffraction pattern substantially as shown in FIGS. 12-20, having characteristic peaks (expressed in degrees two-theta (2θ)) as indicated in Table 2.

TABLE 2

| Form | Degrees two-theta (2θ) |
|---|---|
| I | 9.7, 12.1, 13.2, 14.6, 16.2, 19.3, 20.0, 20.4, 23.8, 24.7, 26.0, 28.4, 30.1 |
| II | 14.5, 15.2, 16.6, 19.0, 23.8, 26.5, 29.9 |
| III | 8.3, 11.9, 13.2, 20.3, 22.1, 23.3, 23.9, 24.7, 26.7, 28.2, 30.7 |
| IV | 8.2, 11.8, 15.2, 16.5, 19.0, 21.7, 22.8, 25.3, 27.7, 30.0 |
| V | 8.8, 12.5, 14.3, 15.6, 17.6, 19.7, 21.0, 21.7, 24.1, 28.7, 30.6 |
| VI | 11.2, 11.9, 12.9, 15.8, 17.4, 18.5, 20.0, 21.3, 22.6, 26.3, 28.7, 30.7 |
| VII | 12.9, 17.0, 19.3, 20.0, 23.6, 25.4, 30.4, 32.2 |
| VIII | 9.5, 11.2, 16.5, 18.8, 20.8, 22.6, 25.7, 27.8, 28.7, 30.2 |
| IX | 10.2, 11.2, 16.7, 18.0, 21.2, 23.0, 25.2, 26.0, 27.6, 29.1, 30.2 |

In some embodiments, the disclosed imidacloprid crystalline forms can be anhydrous and non-solvated. As used herein, "anhydrous" means that the crystalline form contains essentially no bound water in the crystal lattice structure, and the compound does not form a crystalline hydrate.

In some embodiments, the nitroguanidine in IMI can adopt two tautomeric forms between Formula 1A and 1B below.

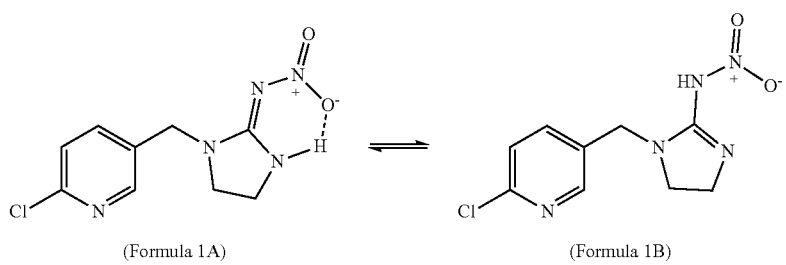

(Formula 1A)  (Formula 1B)

The crystal structure of imidacloprid Form III has been determined under single-crystal X-ray diffraction at 100 K (space group no. P2$_{1/c}$ (14), Z=4, a=11.3264(5) Å, b=10.4652(5) Å, c=9.8634(5) Å, V=1082.56(9) Å$^3$).

The novel imidacloprid polymorphs III, IV, V, VI, VII, VIII, and XI, described herein, may be characterized by powder XRD, Raman spectroscopy, $^1$-NMR, TGA and DSC. Polymorphs I, II, III, IV, VI, VII, VIII, and XI of imidacloprid exhibit a Raman spectra substantially as shown in FIGS. 2-10B, having characteristic peaks (expressed in cm$^{-1}$) as indicated in Table 1.

Figure 22A:
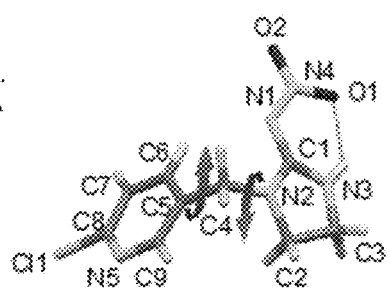
FIGS. 22A, 22B and 22C depict a conformational analysis and relative free energy (AG) of imidacloprid Forms I, II, III, IV, V, VI, VIII, and IX.
Figure 22B:
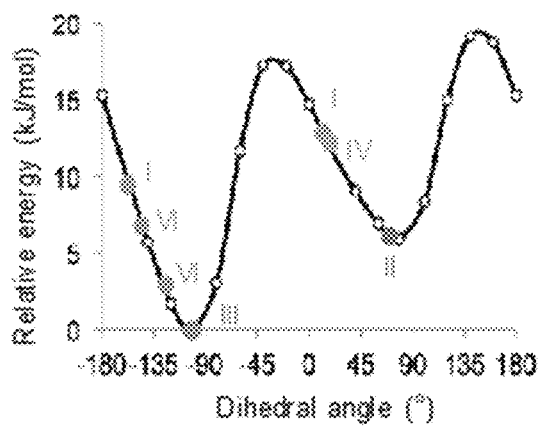

The foremost difference is in the position of one proton. Polymorphs I, II, III, IV, VI, VII, VIII, and XI of imidacloprid contained the tautomer illustrated in Formula 1A, which may be favored by the intramolecular NH . . . O (nitro) hydrogen bond with the nitro group. The alternative tautomer (Formula 1B) is the commonly illustrated imidacloprid and has only one hydrogen bond donor (N—H) but four potential acceptors—two nitro group oxygens, the pyridyl nitrogen, and the exocyclic guanidine nitrogen. The intermolecular hydrogen bonds differ substantially among polymorphs. As shown in FIG. 21, the intermolecular hydrogen bonding can differ among polymorphs I, II, III, IV, VI, VIII, and XI. IMI molecules in Forms I, II, and III are organized as zigzag chains, head-to-head bilayers, and head-to-head columns, respectively. One dimensional intermolecular hydrogen-bonded chains (catemers) adopt a herringbone arrangement in Forms IV, V and VI. Intra- and intermolecular hydrogen bonding between the imidazolidinyl and nitro groups in Forms VIII and IX results in molecular dimers The intramolecular N—H . . . O hydrogen bond observed in polymorphs I, II, III, IV, VI, VII, VIII, and XI forms a pseudo six-membered ring, as shown in Formula 1A, which restricts the conformational freedom about the N1-N4 bond. The preference for one tautomer further restricts the conformational freedom about the N1-C1 bond. FIG. 22A depicts the flexibility primarily arises from the two variable torsional angles defined by C9-C5-C4-N2 and C2-N2-C4-C5 atom sequences between the pyridyl and the imidazolidinyl rings, herein designated as $\theta_{py}$ and $\theta_{imi}$, respectively. The values of torsional angles of IMI molecules in various polymorphs are listed in Table 3 below.

TABLE 3

|  | $\theta_{py}$ (°) | $\theta_{imi}$ (°) |
| --- | --- | --- |
| Form I | −17.75 | −88.65 |
|  | −156.57 | 80.90 |
| Form II | 62.93 | 69.64 |
| Form III | 17.11 | 78.49 |
| Form IV | −26.94 | 98.90 |
| Form V | 106.58 | −70.95 |
| Form VI | 127.37 | −65.3 |
| Form VIII | 146.04 | −67.04 |
|  | 3.51 | 84.99 |
|  | −9.19 | −78.52 |
|  | −40.29 | −70.75 |
| Form IX | −53.26 | −62.58 |
|  | −12.67 | −76.72 |
|  | −11.16 | 94.92 |

In some embodiments, the process for preparing crystalline forms of imidacloprid may implement multiple crystallization methods. Crystallization methods may be used to affect the formation of imidacloprid Forms III, IV, V, VI, VII, VIII, and IX, alone or in mixtures thereof.

In some embodiments, crystalline polymorphs can be prepared by melt recrystallization, for example, by melting imidacloprid Form I. Melting temperatures can range from about 143° C. to about 220° C. In some embodiments, imidacloprid Form I can be positioned on a glass slide for melting. Imidacloprid Form 1 can also be positioned on other glass surfaces, for example, beakers, flasks, capillary tubes, test tubes, and the like. In another embodiment, imidacloprid Form I can be confined between two glass slides for melting.

After melting imidacloprid Form I, crystalline polymorphs can be prepared by cooling the imidacloprid Form I. In some embodiments, the molten imidacloprid can be cooled slowly. The molten imidacloprid can be cooled to an ambient temperature, such as room temperature, or 25° C. In some embodiments, the molten imidacloprid can be maintained at a temperature cooler than the melting point of imidacloprid (143° C.), but above an ambient room temperature, for example, the molten imidacloprid can be maintained at 80° C. or 85° C.

Upon cooling, polymorphs of imidacloprid can be grown from the molten imidacloprid. In some embodiments, crystalline Form IX can grow when cooled and maintained at some temperature between 80° C. and 25° C. In another embodiment, crystalline Form IX can grow when the cooling temperature ranges from about 25° C. to about 85° C.

In some embodiments, as shown in FIG. 23, the process for preparing crystalline polymorphs can comprise seeding crystals at various temperatures. For example, single crystals of Forms III, IV, V, VII, and IX can be obtained by crystallization from the melt using respective seed crystals. In another embodiment, a process for preparing crystalline Form VI can comprise seeding the molding imidacloprid with Form III crystals to grow Form VI.

Figure 24A:
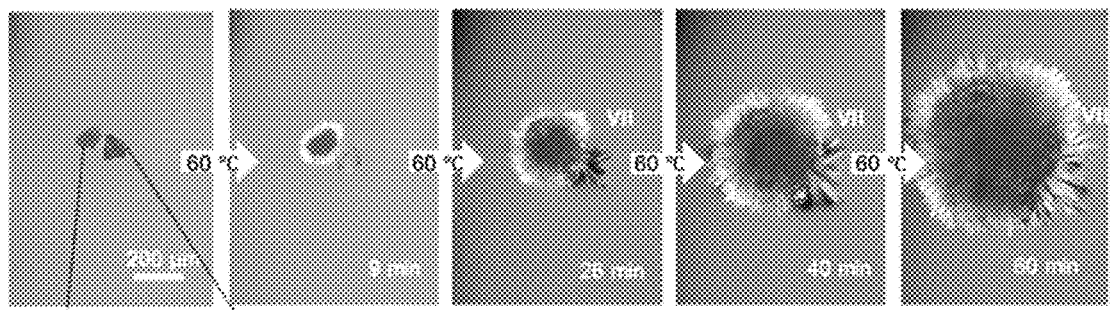
FIGS. 24A-24C show the preparation of imidacloprid single crystals Form VII confined in controlled pore glass, in accordance with the exemplary embodiment of the present disclosure.
Figure 24B:
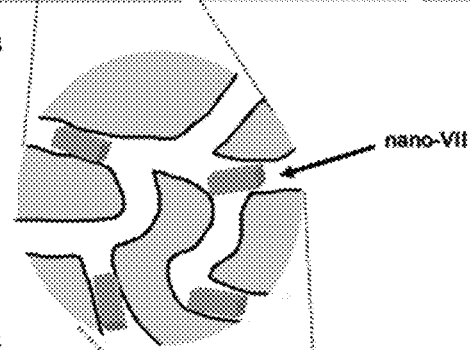
Figure 24C:
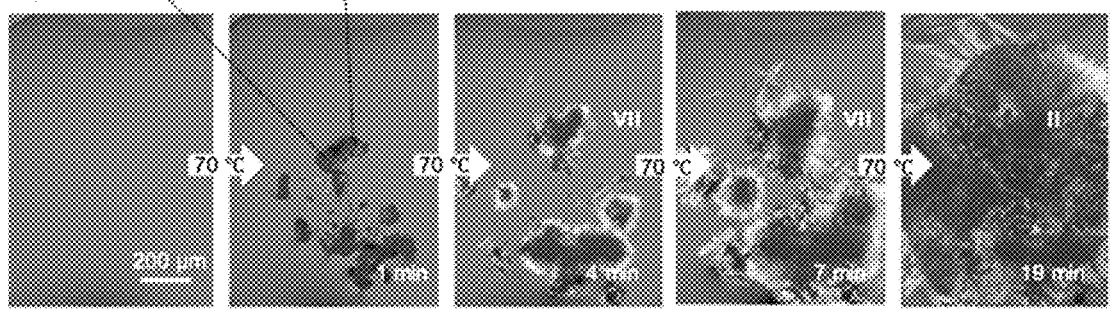
Figure 25A:
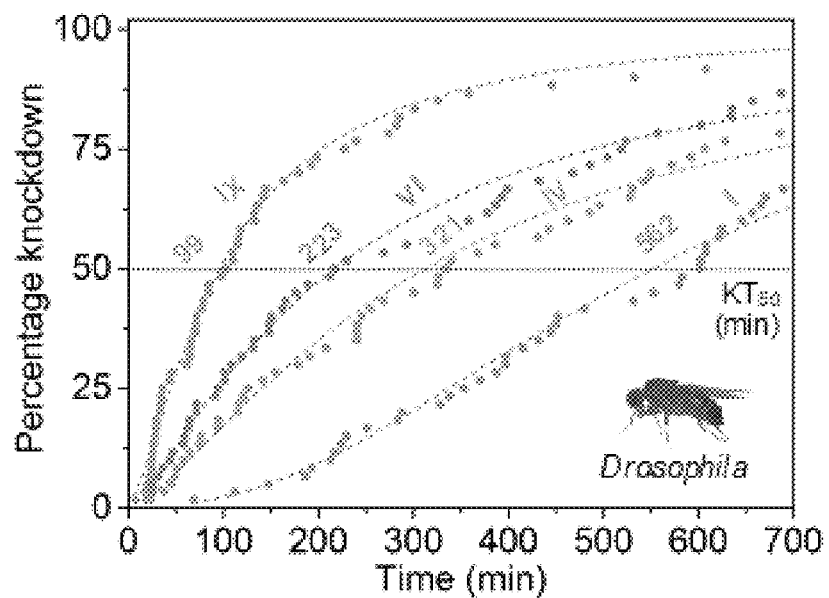
FIG. 25A shows a graph comparing lethality in percentage knockdown v. time (min) of imidacloprid Forms I, IV, VI, and IX on *Drosophila melanogaster*.
Figure 25B:
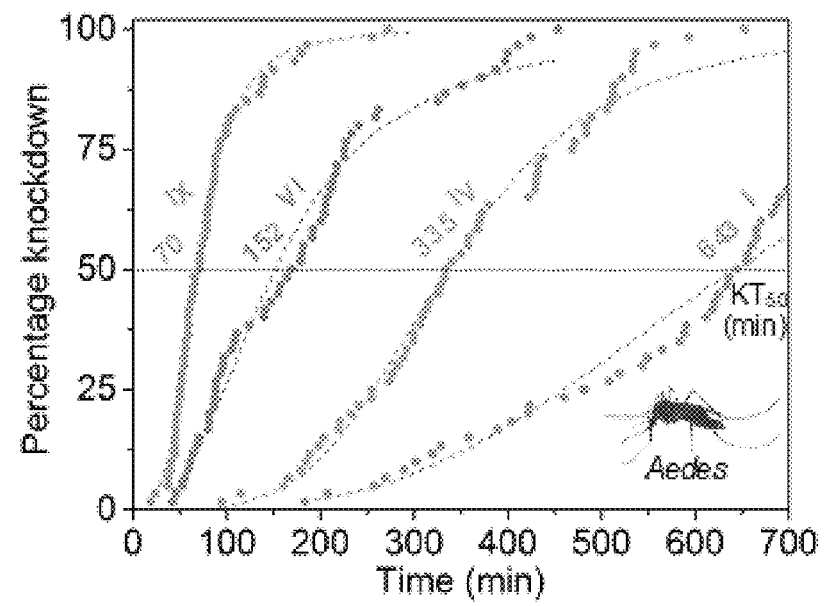
FIG. 25B shows a graph comparing lethality in percentage knockdown v. time (min) of imidacloprid Forms I, IV, VI, and IX on *Aedes qegypti*.
Figure 25C:
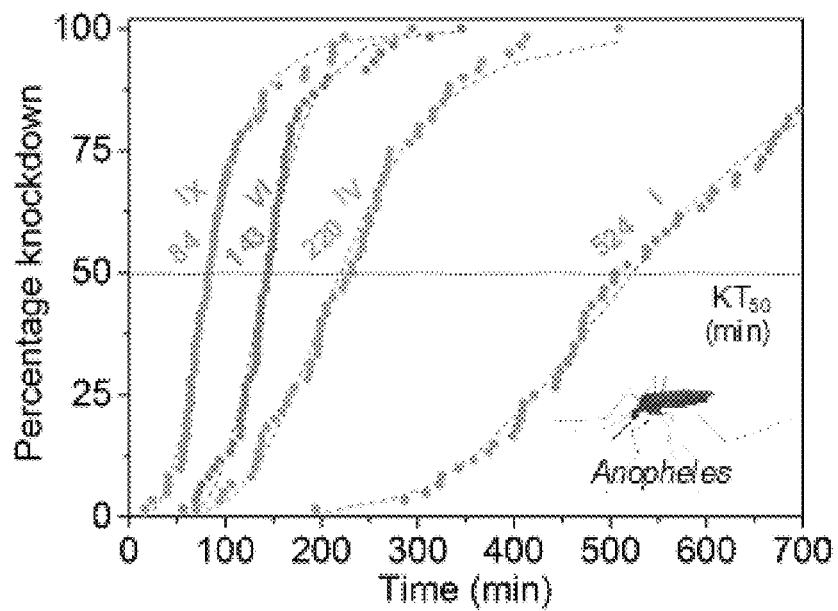
FIG. 25C shows a graph comparing lethality in percentage knockdown v. time (min) of imidacloprid Forms I, IV, VI, and IX on *Anopheles*.
Figure 25D:
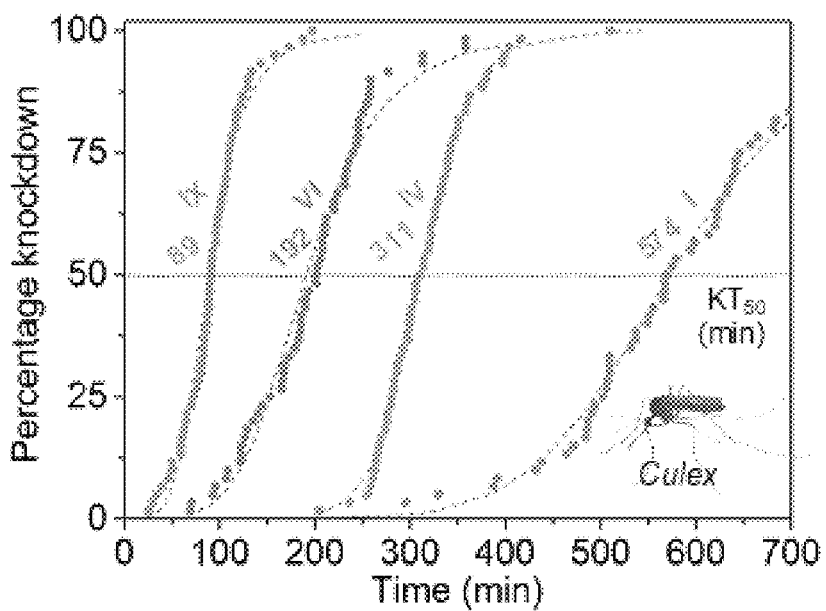
FIG. 25D shows a graph comparing lethality in percentage knockdown v. time (min) of imidacloprid Forms I, IV, VI, and IX on *Culex*.

In another embodiment, as shown in FIG. 24, the process for preparing crystalline polymorphs can comprise nanoconfinement. For example, the process for preparing crystalline polymorph VII can comprise, prior to cooling imidacloprid Form I, pouring molten imidacloprid into a porous media. Porous media can include, but not be limited to, controlled pore glass, mesoporous silica, molecular organic frameworks, porous polymer, porous carbon, carbon nanotubes, microfluidic thin films, heterogeneous porous media, and combinations thereof.

In some embodiments, a process for preparing crystalline Form V or Form III may comprise a step of phase transforming Form IX into either crystalline Form V or Form III.

In some embodiments, a process for preparing crystalline polymorphs may comprise dissolving imidacloprid Form I in an appropriate amount of aqueous solvent or a mixture of solvents to obtain an aqueous solution. The term "aqueous solvent or mixture of solvents" as used herein means water, methanol, ethanol, tetrahydrofuran, acetonitrile, methylene chloride, isopropyl alcohol, acetone, N,N-dimethyl-Formamide, dimethyl sulfoxide, or a combination thereof. In some embodiments, a process for preparing imidacloprid Form IV can comprise combining imidacloprid Form I with ethanol or another solvent. In some embodiments, combining imidacloprid Form I with ethanol can result in dissolving some or all of the imidacloprid Form I, such that a solution of imidacloprid-saturated ethanol is formed. Dissolving can be done under increased temperatures or ambient temperatures. The process for preparing imidacloprid Form IV may further comprise evaporating the ethanol. Evaporation can be through maintaining an increased temperature or through air movement about the sample. In some embodiments, the process for preparing imidacloprid Form IV may comprise cooling the imidacloprid-saturated ethanol solution rapidly. In another embodiment, the imidacloprid-saturated ethanol solution can be cooled slowly. From the imidacloprid-saturated ethanol solution, crystals of Form IV may grow.

Solution crystallization of imidacloprid Form I can be obtained from a variety of organic solvents, while Form II and a new polymorph, Form IV, can be obtained from acetone and ethanol solutions as indicated in Table 4 below.

TABLE 4

| Solvent | IMI |
| --- | --- |
| Ethyl acetate | Form I |
| Diethyl ether | Form I |
| Toluene | Form I |
| Acetone | Form II |
| Ethanol | Form IV |
| Methanol | Form I |
| Dichloromethane | Form I |
| Chloroform | Form I |
| Hexane | Form I |
| Acetonitrile | Form I |
| Methyl propionate | Form I |
| Dimethylformamide | Form I |
| Pyridine | Form I |
| Water | Form I |

A process for preparing the crystalline Form III may comprise growing crystals of imidacloprid Form IX using the melt crystallization methods as described above, and phase transforming imidacloprid Form IX into crystalline Form III. The process for preparing crystalline Form III may further comprise cross-nucleation with another polymorph. For example, in some embodiments, cross-nucleation can take place with crystalline Form V. In some embodiments, cross-nucleation can occur at an increased temperature or at an ambient temperature, such as room temperature or 25° C.

In some embodiments, the crystalline forms of the invention can be substantially isolated. As used herein, "substantially isolated" is meant that a particular crystalline form of imidacloprid is at least partially isolated from impurities. For example, in some embodiments a crystalline form of imidacloprid comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated crystalline form including, for example, other crystalline forms and other substances.

In some embodiments, a crystalline form of imidacloprid can be substantially free of other crystalline forms. The phrase "substantially free of other crystalline forms" means that a particular crystalline form of imidacloprid can comprise greater than about 80%, greater than about 90%, greater than about 95%, greater than about 98%, greater than about 99% or greater than about 99.5% by weight of the particular crystalline form.

In another aspect, a pesticidal composition can comprise the crystalline forms of imidacloprid, including one of Forms III, IV, V, VI, VII, VIII, XI, and combinations thereof. As used herein the term "pesticidal composition" refers to a composition comprising a substance or mixture of substances capable of expelling, killing, destroying, exterminating, preventing, or mitigating any pest.

In any particular embodiment, a composition is administered in an effective amount. That amount may depend on a variety of factors, including (but not limited to) the area to be treated, the pest to be treated, its metabolism, its behavior (e.g., feeding habits, breeding, daily or seasonal activity cycles, development, nesting habits, etc.), and behavior of the host the pest infests.

As used herein the term "effective" applied to dose or amount refers to that quantity of a pesticide that is sufficient to result in a desired pesticidal action or activity.

In general, the effective dose of imidacloprid Form I can range from about 10 to 25 mg pesticide per kg insect, host, or soil. In some embodiments, effective doses of imidacloprid polymorphs III, IV, V, VI, VII, VIII, and IX can be substantially less than the effective dose of imidacloprid Form I. For example, in some embodiments one or more crystalline forms of imidacloprid can comprise less than about 10 mg pesticide per kg locus, host, or soil, less than about 5 mg, less than about 2 mg, less than about 1 mg, less than about 100 µg, less than about 10 µg, or less than about 1 µg of pesticide per kg locus, host, or soil. Said another way, in some embodiments, one or more crystalline forms of imidacloprid can range from about 10 parts per million (ppm) to about 1 part per billion (ppb).

In certain embodiments, the rates of concentration of imidacloprid polymorphs are in the range from about 0.01 to about 1000 ppm (parts-per-million), such as from about 0.1 to about 500 ppm of each active ingredient. In area-wide applications, rates of application per hectare may be from about 0.5 g/ha to 2000 g/ha, such as particularly from about 10 to 1000 g/ha, or from about 20 to 600 g/ha. As one non-limiting example, pesticides for the control of mosquito vectors of malaria may be used in area-wide applications at a rate of application of about 70 g/ha to about 1.15 kg/ha.

In some embodiments, the pesticidal composition comprising one or more crystalline forms selected from Forms III, IV, V, VI, VII, VIII, XI of imidacloprid can be present in the composition in an amount of about 0.01% to about 75% by weight.

In some particular embodiments, the pesticidal composition comprising one or more crystalline forms selected from Forms III, IV, V, VI, VII, VIII, XI of imidacloprid can be present in the composition in an amount of about 0.5% to about 75% by weight.

In one embodiment, the present invention provides the pesticidal composition, wherein the crystalline form is present in the composition in an amount of about 0.01% to about 90% by weight, or about 0.1% to about 80% by weight, or about 0.5% to about 75% by weight, or about 0.5% to about 5% by weight, or about 15% to about 25% by weight, or about 21% by weight to about 22% by weight, or about 70% to about 80% by weight, or about 0.5%, or about 21%, or about 75%, by weight.

As shown in FIGS. 25A-25D, imidacloprid polymorphs, including Forms IV, VI, and IX, as well as polymorphs not illustrated in FIGS. 25A-25D, and compositions comprising any imidacloprid polymorph disclosed herein may be used as agents to control pests, i.e. as pesticides and/or pest repellents. Any of the imidacloprid forms disclosed herein may be effective to control a pest. As used herein, "pests" means any animal or plant harmful to humans or human concerns. Pests can include, without limitation, the following pests described according to taxonomic designation and/or vernacular name:

Order Acarina, including *Acarus siro, Aceria sheldoni, Aculus schlechtendali, Amblyomma* species, *Argas* species, *Boophilus* species, *Brevipalpus* species, *Bryobia praetiosa, Cahpitrimerus* species, *Chorioptes* species, *Dermanyssus gallinae, Eotetranychus carpini, Eriophyes* species, *Hyalomma* species, *Ixodes* species, *Olygonychus pratensis, Ornithodoros* species, *Panonychus* species, *Phyllocoptrum oleivora, Polyphagotarsonemus latus, Psoroptes* species, *Rhipicephalus* species, *Rhizoglyphus* species, *Sarcoptes* species, *Tarsonemus* species, *Tetranychus* species, *Dermacentor* species, *Aponomma* species, and *Haemaphysalis* species.

Order Homoptera, including *Aleurothrixus floccosus, Aleyrodes brassicae, Aonidiella* species, *Aphididae* species, *Aphis* species, *Aspidiotus* species, *Bemisia tabaci, Ceroplaster* species, *Chrysomphalus aonidium, Chrysomphalus dictyospermi, Coccus hesperidum, Empoasca* species, *Eriosoma lanigerum, Erythroneura* spp, *Gascardia* species, *Laodelphax* species, *Lecanium corni, Lepidosaphes* species, *Macrosiphus* species, *Myzus* species, *Nephotettix* species, *Nilaparvata* species, *Paratoria* species, *Pemphigus* species, *Planococcus* species, *Pseudaulacaspis* species, *Pseudococcus* species, *Psylia* species, *Pulvinaria aethiopica, Quadraspidiotus* species, *Rhopalosiphum* species, *Saissetia* species, *Scaphoideus* species, *Schizaphis* species, *Sitobion* species, *Trialeurodes vaporariorum, Trioza erytreae, Unaspis citri*; and *Homalodisca coagulata;*

Order Hymenoptera, including Family Formicidae, Family Apidae, and Family Bombidae, such as *Acromyrmex* species, *Atta* species, *Cephus* species, *Diprion* species, *Diprionidae* species, *Gilpinia polytoma, Hoplocampa* species, *Lasius* species, *Monomorium pharaonis, Neodiprion* species, *Solenopsis* species, and *Vespa* species;

Order Diptera, including Family Culicidae, Family Simulidae, Family Psychodidae, Family Ceratopogonidae, Family Sarcophagidae, Family Streblidae, and Family Nycteribiidae, such as *Aedes* species, *Antherigona soccata*, *Bibio hortulanus*, *Calliphora erythrocephala*, *Ceratitis* species, *Chrysomyia* species, *Culex* species, *Culex p. pipiens*, *Cuterebra* species, *Dacus* species, *Drosophila* species, *Fannia* species, *Gastrophilus* species, *Glossina* species, *Hypoderma* species, *Hyppobosca* species, *Liriomyza* species, *Lucilia* species, *Melanagromyza* species, *Musca* species, *Oestrus* species, *Orseolia* species, *Oscinella frit*, *Pegomyia hyoscyami*, *Phorbia* species, *Rhagoletis pomonella*, *Sciara* species, *Stomoxys* species, *Tabanus* species, *Tannia* species, and *Tipula* species;

Order Siphonaptera, including *Ceratophyllus* species, *Xenopsylla cheopis* and other *Xenopsylla* species, *Ctenocephalides* species, *Oropsylla* species, *Pulex* species, *Opisocrostis* species, *Echidnopaga* species, and *Diamanus* species;

Order Thysanura, including *Lepisma saccharina*;

Order Lepidoptera; including *Acleris* species, *Adoxophyes* species, *Aegeria* species, *Agrotis* species, *Alabama argulaceae*, *Amylois* species, *Anticarsia gemmatalis*, *Archips* species, *Argyrotaenia* species, *Autographa* species, *Busseola fusca*, *Cadra cautella*, *Carposina nipponensis*, *Chilo* species, *Choristoneura* species, *Clysia ambigueua*, *Cnaphalocrocis* species, *Cnephasia* species, *Cochylis* species, *Coleophora* species, *Crocidolomia binotaus*, *Cryptophlebia leucotreta*, *Cydia* species, *Diatraea* species, *Diparopsis castanea*, *Earias* species, *Ephestia* species, *Eucosma* species, *Eupoecilia ambiguena*, *Euproctis* species, *Euxoa* species, *Grapholila* species, *Hedya nubiferana*, *Heliothis* species, *Hellula andalis*, *Hyphantria cunea*, *Keiferia lycopersicella*, *Leucoptera scitella*, *Lithocllethis* species, *Lobesia botrana*, *Lymantria* species, *Lyonetia* species, *Malacosoma* species, *Mamestra brassicae*, *Manduca sexta*, *Operophtera* species, *Ostrinia nubilalis*, *Pammene* species, *Pandemis* species, *Panolisflammea*, *Pectinophora gossypieua*, *Phthorimaea operculeua*, *Pieris rapae*, *Pieris* species, *Plutella xylostella*, *Prays* species, *Scirpophaga* species, *Sesamia* species, *Sparganothis* species, *Spodoptera* species, *Synanthedon* species, *Thaumetopoea* species, *Tortrix* species, *Trichoplusia ni*, and *Yponomeuta* species;

Order Coleoptera, including *Agriotes* species, *Anthonomus* species, *Atomaria linearis*, *Chaetocnema tibialis*, *Cosmopolites* species, *Curculio* species, *Dermestes* species, *Diabrotica* species, *Epilachna* species, *Eremnus* species, *Leptinotarsa decemlineata*, *Lissorhoptrus* species, *Melolontha* species, *Oryzaephilus* species, *Otiorhynchus* species, *Phlyctinus* species, *Popillia* species, *Psylliodes* species, *Rhizopertha* species, *Scarabeidae*, *Sitophilus* species, *Sitotroga* species, *Tenebrio* species, *Tribolium* species, and *Trogoderma* species;

Order Orthoptera, including *Blatta* species, *Blattella* species, *Gryllotalpa* species, *Leucophaea maderae*, *Locusta* species, *Periplaneta* species, and *Schistocerca* species;

Order Isoptera, including *Reticulitermes* species;

Order Psocoptera, including *Liposcelis* species;

Order Anoplura, including *Haematopinus* species, *Phthirus pubis* and other *Phthirus* species, *Linognathus* species, *Pediculus* species, *Pemphigus* species, and *Phylloxera* species;

Order Mallophaga, including *Damalinea* species and *Trichodectes* species;

Order Thysanoptera, including *Frankliniella* species, *Hercinothrips* species, *Taeniothrips* species, *Thripspalmi*, *Thrips tabaci* and *Scirtothrips aurantii*;

Order Heteroptera, including *Cimex* species, *Distantiella theobroma*, *Dysdercus* species, *Euchistus* species, *Eurygaster* species, *Leptocorisa* species, *Nezara* species, *Piesma* species, *Rhodnius* species, *Sahlbergella singularis*, *Scotinophara* species and *Triatoma* species;

Order Scopriones, including *Centruriodes* species, *Euscorpius* species, *Parabuthus* species, and *Vaejovis* species;

Order Araneae, including *Latrodectus* species, *Loxosceles* species, and *Brachypelma* species;

Order Hemiptera, including *Cimicidae* species, *Enicocephalidae* species, *Pentatomidae* species, *Gerridae* species, *Saldidae* species, *Belostomatidae* species, and *Nepidae* species;

Class Diplipoda (millipedes); and

Class Chilopoda (centipedes).

In some embodiments, the pest can be a member of the taxonomic order or subclass Acarina, including soft and hard ticks; Diptera, including *Tabanidae*, anophelines, and culecines; or Siphonoptera. In other particular embodiments, the pest can belong to a particular species, such as *Ixodes scapularis* (deer tick), *Aedes aegypti* (mosquito), *Xenopsylla cheopis* (rat flea), *Homalodisca coagulata* (glassy-winged sharpshooter), or *Culex pipiens* (mosquito).

Other exemplary arthropod pests and/or parasites include fleas; mosquitoes; bees, yellow jackets, and wasps; cockroaches, including the American and German cockroach; termites; houseflies and silverleaf whiteflies; lacey-winged sharpshooters or glassy-winged sharpshooters; leaf hoppers, such as the grape or potato leafhoppers; cabbage looper (Lepidoptera); ants, such as the pharaoh ant, argentine ant, carpenter ant, and fire ant; stink or lygus bugs; leafminers; western flower thrips; aphids, such as melon aphids and black bean aphids; arachnids, such as spiders, ticks, and plant mites, including two-spotted spider mites, McDaniel mites, Pacific mites, and European mites.

In one embodiment, the pest is an insect selected from adelgids, ants, aphids, annual bluegrass weevil (adults), azalea lace bugs, bagworms, bees, bed bugs, billbugs (adults), blue bottle flies, black turfgrass ataenius (adults), boxelder bugs, brown, marmorated stink bug, cankerworms, cardamom thrips, carpenter ants, carpenter bees, carpet beetles, centipedes, cecid flies, chinch bugs, clothes moths, clover mites, cluster flies, cockroaches, crickets, darkling beetles, dermestids, earwigs, elm leaf beetles, elm spanworms, European pine sawflies, fall webworms, firebrats, fleas(indoors & outdoors), flea beetles, flies, flesh flies, fruit flies, fungus gnats (sciarid flies), gnats, grasshoppers, green bottle flies, greenstriped mapleworms, ground beetles, grubs, gypsy moths (larvae), hide beetles, house flies, hornets, horseflies, houseflies, imported willow leaf beetles, Indian meal moth, Japanese beetles, June beetles (adults), killer bees, leafhoppers, leaf-feeding caterpillars, leaf skeletonizers, leaf rollers, leather beetles, lice, loopers, maize weevils, mealybugs, medflies, midges, millipedes, mimosa webworms, mites, mole crickets, moths, mosquitoes, multicolored Asian lady beetles, orange-striped oakworms, pantry beetles, pantry moths, pillbugs, pine shoot beetles, pine tip moths, pinyon spindlegall midges, plant bugs, pharaoh's ants, phorid flies, redhumped caterpillar, red imported fire ants, red flour beetles, rice weevils, saw-toothed grain beetle, sawfly larvae, scale insects (crawlers), scorpions, silverfish, spiders, sod webworms, sowbugs, springtails, stable flies, pantry pests, stored product pests, tent caterpillars, ticks (indoors & outdoors), yellowjackets, yellow-necked caterpillar, wasps, webworms.

Imidacloprid polymorphs including Forms III, IV, V, VI, VII, VIII, and IX, or compositions comprising any polymorph of imidacloprid described herein can be applied directly to the pest, thus causing the pest to directly contact the composition. In another embodiment, the imidacloprid polymorphs may be applied to some locus or host that is expected to come into contact with the pest. If applied to a locus, imidacloprid polymorphs and/or a composition comprising imidacloprid polymorphs may be applied to the locus generally, such as by an aerosol or fumigant, or applied to a human, non-human animal, plant, or inanimate object within that locus. The size of a particular locus may vary considerably according to the method of application. For example, in area-wide applications, imidacloprid polymorphs and/or a composition comprising imidacloprid polymorphs can be dispersed over a locus of an environment, rather than intentionally directed at a particular pest, human, plant, or inanimate object. The locus of an area-wide application may be several hundred to thousands of acres, if imidacloprid polymorphs and/or a composition comprising one or more imidacloprid polymorphs are used for agricultural spraying or to control the spread of a vector-borne disease; in structural applications, such as controlling pests within a home or restaurant, the locus may be several hundred several thousand square feet. However, in personal, veterinary, or horticultural applications, such as using topical pest repellent spray or ointment, or using a flea shampoo to bathe a pet, the locus may be limited to the area in the immediate vicinity of the animal, plant, or human host.

When used as a contact insecticide, the effectiveness of imidacloprid relies on physical contact between its crystal surfaces and insect tarsi. Anticipating that insect uptake of imidacloprid molecules would depend on the respective free energies of surfaces of crystalline polymorphs, measurements of insect knockdown times for the metastable crystal forms revealed an efficacy improvement as much as nine times against *Aedes*, *Anopheles*, and *Culex* mosquitoes as well as *Drosophila* (fruit flies). Epidemiological modelling suggests that replacing commercially available imidacloprid crystals (a.k.a. Form I) in space spraying with any one of the new polymorphs disclosed herein would significantly suppress dengue transmission, even in the presence of high levels of resistance, while reducing the harm to non-target organisms.

Methods of application include dusting, spraying, atomizing, immersing, coating, dressing, scattering, and pouring. A particular method of application may be selected in accordance with the intended objectives of and circumstances related to a particular use.

The frequency of application also may depend on the residual action of imidacloprid polymorphs Forms III, IV, V, VI, VII, VIII, and IX. "Residual action" refers to the length of time a compound or composition may exist in a particular environment and remain effective. Imidacloprid polymorphs and/or the compositions comprising one or more imidacloprid polymorphs described herein may be employed in formulations intended for use in public or private homes, residences, businesses, restaurants, hospitals, or other similar places of human activity. In such embodiments, the formulations may be used to kill or repel pests, such as mosquitoes, ants, spiders, or roaches, and may be applied directly to the pests or a locus the pest is expected to contact. For example, flea bomb or other fumigant containing imidacloprid polymorphs as an active ingredient could be used within a home (such as applied within a particular room of a home to control fleas). As another example, a commercial spray containing imidacloprid polymorphs as an active ingredient could be applied to the floors and other interior spaces of a restaurant to control cockroaches. In any such embodiment, the formulation may kill or repel a pest by directly contacting the pest, may be induced into the atmosphere of the locus, or may be applied to a human, non-human animal, plant, or inanimate object (e.g., the surface of a floor) expected to come into contact with the pest. Crystalline imidacloprid may be used on mosquito nets to which solid particles have been adhered.

Certain embodiments employ formulations for use on humans, non-human animals, or plants for their protection. For example, certain formulations may be insecticides and/or acaricides sprayed onto the leaves of indoor plants for controlling aphids. Other formulations may include lotions or oils that repel pests.

In some embodiments, imidacloprid polymorphs including Forms III, IV, V, VI, VII, VIII, and IX, or compositions comprising any polymorph of imidacloprid described herein can be applied once, while alternative embodiments employ plural applications of the same composition or different compounds or compositions. In particular embodiments, a composition is administered on an hourly, daily, weekly, monthly, quarterly, or annual basis. In any particular embodiment, the frequency of application may be regular or irregular, and the time elapsed between successive applications may be the same or different. For example, and without limitation, imidacloprid polymorphs and/or a composition comprising imidacloprid polymorphs may be applied every eight to twelve hours; four times per day at irregular intervals; every evening; four times per week; every other day; every other week; every other month; twice a month; every three months; every six months; every nine months; or annually. Like the amount of the compound or composition used in an embodiment, the frequency and number of applications of that compound or composition may depend on a variety of factors, including (but not limited to) the area to be treated, the pest to be treated, its metabolism, and its behavior (e.g., feeding habits, breeding, daily or seasonal activity cycles, development, nesting habits, etc.), and behavior of the host the pest infests.

Use of pesticides is regulated in the United States by state and federal agencies, including the Environmental Protection Agency (EPA) and Food and Drug Administration (FDA). Relevant regulatory programs include the Federal Insecticide, Fungicide and Rodenticide Act (FIFRA) and the Federal Food, Drug and Cosmetic Act (FD&C Act). Certain articles of manufacture in accordance with these governmental and regulatory considerations may be made using disclosed pest control compositions comprising imidacloprid Forms III, IV, V, VI, VII, VIII, and/or IX.

EXAMPLES

The following examples are provided by way of illustration. The examples should not be construed as limiting, as the examples merely provide specific understanding and practice of the embodiments and their various aspects.

Methods. Crystallization of IMI polymorphs. Single crystals of IMI Forms II, and IV were prepared in 20 mL glass vials by slow evaporation from saturated acetone and ethanol solutions at ambient temperature, respectively. Alternatively, Form IV could be prepared by seeding crystalline clothianidin in its commercial form to the IMI melts at 60-100° C. Forms III and V were prepared by phase transformations from Form IX at RT. Single crystals of Form VI were prepared by seeding Form III crystals in to the melts at 70-100° C. Nano-Form VII was prepared by nanoconfinement of the melts using controlled pore glass (CPG, pore size=35, 100, or 200 nm) at 180° C. on DSC, then cooling to ambient temperature. The bulk Form VII was obtained by seeding nano-Form VII confined in CPG to the melt at 60° C. Forms VIII and IX were prepared by holding the supercooled melt on glass slides at 25-80° C. and 85° C., respectively. Single crystals of IMI polymorphs for X-ray analysis were prepared by placing small single crystal seeds of respective polymorphs in contact with a supercooled melt, then heating the melt at various temperatures on a hot stage.

Lethality measurements for IMI polymorphs. Microcrystals of IMI Forms I, IV, VI, and IX were prepared by grinding respective single crystals using a mortar and pestle. Their compositions were then analyzed by powder X-ray diffraction (PXRD). Lethality measurements were performed in triplicate for each solid-state form, each accompanied by three controls (no insecticide). 2.0 mg of microcrystals was added to a 35 mm diameter polystyrene petri dish, which was subsequently shaken to disperse the microcrystals throughout the petri dish. Microcrystals was added to a polystyrene petri dish (2.000 mg microcrystals per 35 mm diameter dish for fruit flies; 0.100 mg microcrystals per 100 mm diameter dish for mosquitoes), which was subsequently shaken to disperse the microcrystals throughout the petri dish. Adult mosquitoes (*Ae. aegypti, A. quadrimaculatus* or *C. quinquefasciatus*) or fruit flies (*D. melanogaster*) were sedated with carbon dioxide and 30 female mosquitoes or 20 flies were transferred to each petri dish. The top of the dish was then placed over the bottom and the motion of the insects was recorded with a video camera (Sony HDR-CX455). The knockdown time was measured for each individual insect, with knockdown associated with an insect laying on the bottom surface of the petri dish in a supine position without moving from its original position after 10 seconds.

Statistical analyses. Logistic regression of knockdown-time curves was preformed to obtain the median knockdown time (KT50) of the test flies and mosquitoes, the 95% confidence intervals (CI), slopes, and standard errors (SE) using Qcal software.

Materials. Imidacloprid (IMI, 1-[(6-chloro-3-pyridinyl)-methyl]-N-nitro-2-imidazolidinimine) and clothianidin (1-(2-chl oro-1,3-thiazol-5-ylmethyl)-3-methyl-2-nitroguanidine) were purchased from Sigma Aldrich and used as supplied. All solvents were purchased from Sigma Aldrich or Fischer Chemical and used as supplied. Fruit flies (*Drosophila melanogaster*) were raised in-house using standard protocols. Adults of *Anopheles quadrimaculatus, Aedes aegypti*, and *Culex quinquefasciatus* were purchased from Benzon Research. The *Aedes aegypti* colony at Benzon Research was derived from the USDA "Gainesville" strain and has been continuously colonized at Benzon Research since 1994. The *Anopheles quadrimaculatus* colony at Benzon Research was originally sourced from the USDA in Gainesville and has been continuously colonized at Benzon Research since 2011.

Raman spectroscopy. Raman spectra were recorded on a Raman microscope (DXR, Thermo Fisher Scientific, Waltham, Mass.) using a 532 nm excitation laser operating at 2 mW, with a 2 cm$^{-1}$ resolution and slit width of 50 μm. The data was analyzed using the Omnic software package.

Differential scanning calorimetry (DSC). DSC measurements were performed on a Perkin Elmer DSC 8000. The data was analyzed using the Perkin Elmer software package.

Polarized light microscopy. A microscope fitted with crossed polarizers (Olympus BX50) and equipped with a digital camera was used to record crystallization. A microscope hot stage (Mettler FP82HT) was used for temperature control.

X-ray powder diffraction. X-ray microdiffraction (μ-XRD) was performed on a Bruker D8 Discover GADDS Microdiffractometer equipped with a VÅNTEC-2000 two-dimensional (2D) detector and a sealed Cu X-ray tube. The X-ray beam was monochromated with a graphite crystal and collimated with a 0.5 mm MONOCAP, which provided a focused spot beam (λ=1.54178 Å). The sample was loaded into a 0.8 mm Kapton capillary or onto a silicon chip for data acquisition. Two scans were performed with the φ angle rotating and $θ_1$ (incident angle of the X-ray beam)=$θ_2$ (detector angle)=12°. The sample-to-detector distance was 150 mm and the exposure time was 20 minutes. One-dimensional (1D) diffraction patterns were generated by integrating the 2D XRD images over the entire range of azimuthal angles spanning 5°≤2θ≤35° range using the XRD$^2$EVAL program (version 2009.5-0; Bruker AXS Inc., Madison, Wis., 2009).

Single-crystal structure determination. X-ray intensity data for DFDT and MFDT crystalline forms were recorded on a Bruker D8 APEX-II CCD system with the ω scan method at 100 K using graphite-monochromated and 0.5 mm MonoCap-collimated Mo-Kα radiation (λ=0.71073 Å). The temperature was controlled by an Oxford Cryosystems 700+ Cooler. The data sets were processed with the INTEGRATE program of the APEX2 software for reduction and cell refinement. Multi-scan absorption corrections were applied by the SCALE program for the area detector. Both structures were solved by intrinsic phasing methods (SHELXT) and the structure models were completed and refined using the full-matrix least-square methods on F$^2$ (SHELXL). Non-hydrogen atoms in the structures were refined with anisotropic displacement parameters, and hydrogen atoms on carbons were placed in idealized positions (C—H=0.95-1.00 Å) and included as riding with $U_{iso(H)}$=1.2 or 1.5 $U_{eq(non-H)}$. The selected crystallographic parameters were listed in Table 7.

Example 1: New Polymorphs of Imidacloprid

Figure 2:
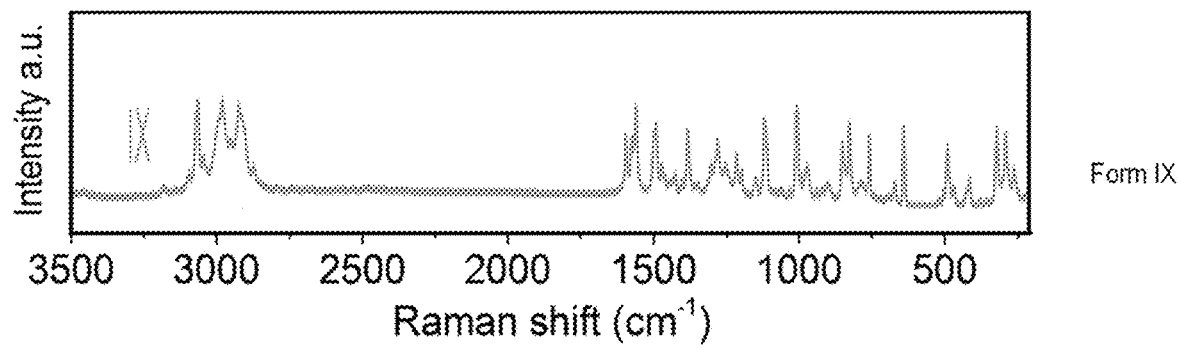
FIG. 2 shows a Raman spectrum of imidacloprid Form IX.
Figure 3:
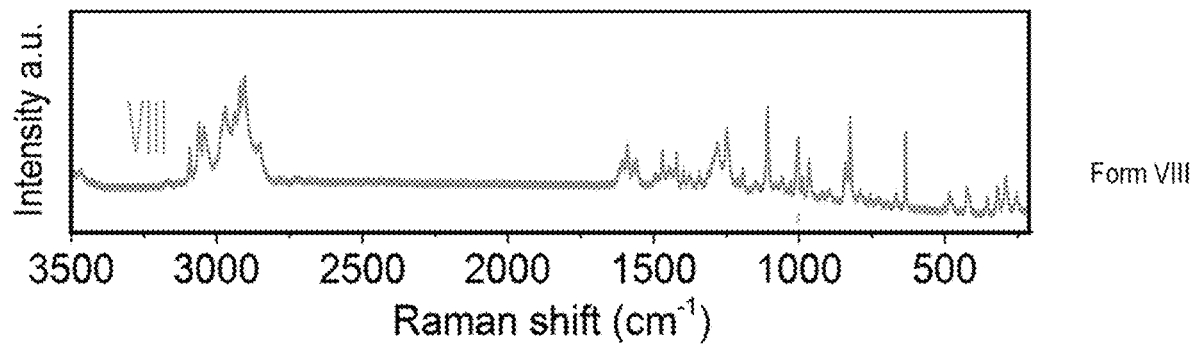
FIG. 3 shows a Raman spectrum of imidacloprid Form VIII.
Figure 4:
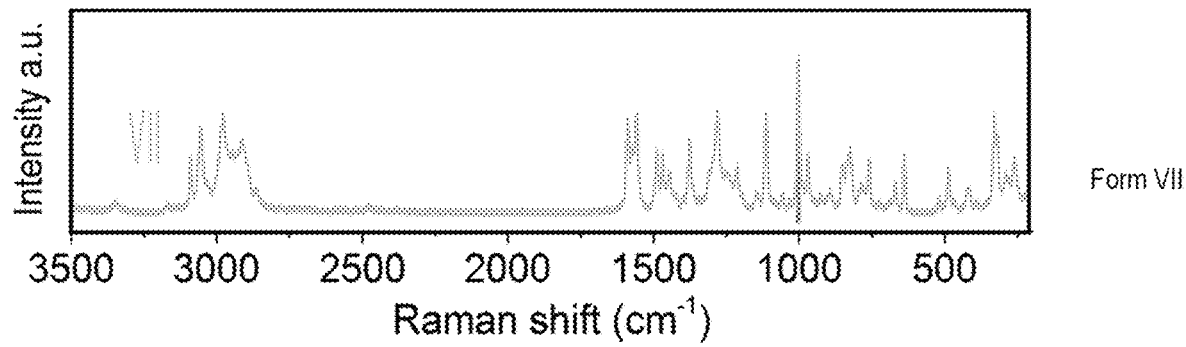
FIG. 4 shows a Raman spectrum of imidacloprid Form VII.
Figure 5:
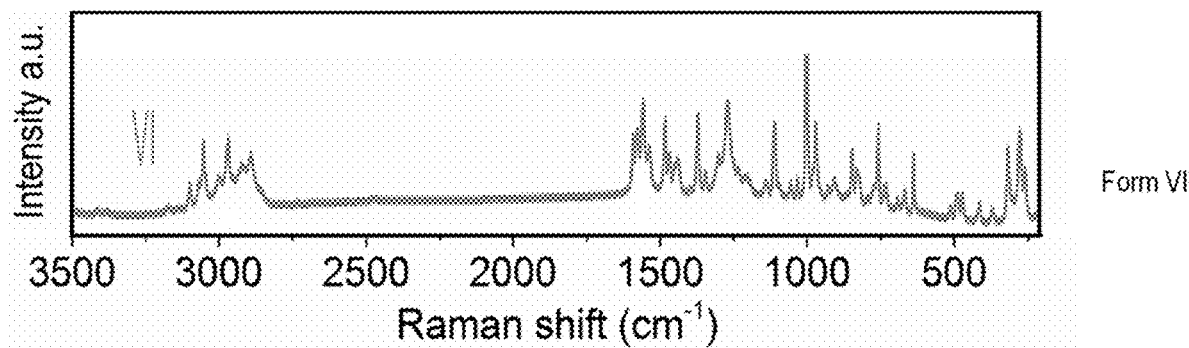
FIG. 5 shows a Raman spectrum of imidacloprid Form VI.
Figure 6:
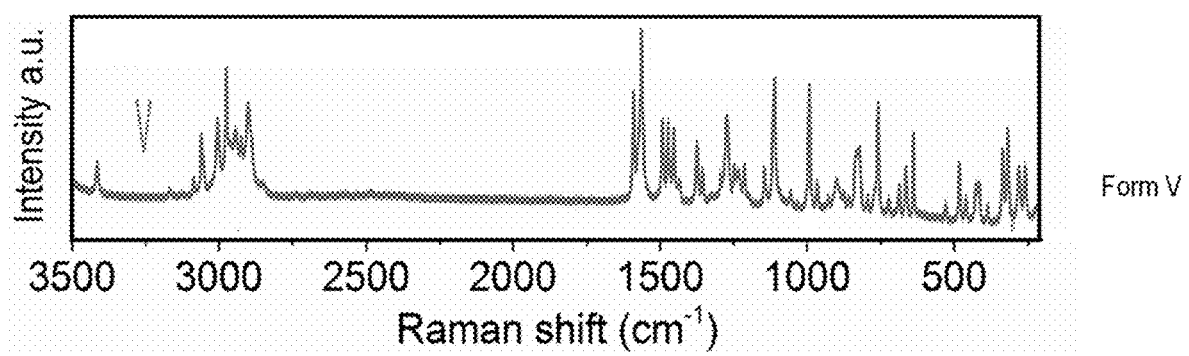
FIG. 6 shows a Raman spectrum of imidacloprid Form V.
Figure 7:
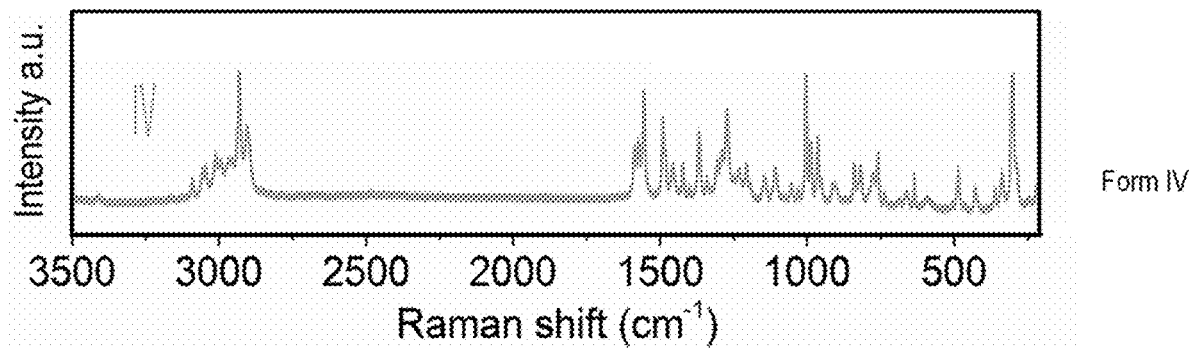
FIG. 7 shows a Raman spectrum of imidacloprid Form IV.
Figure 8:
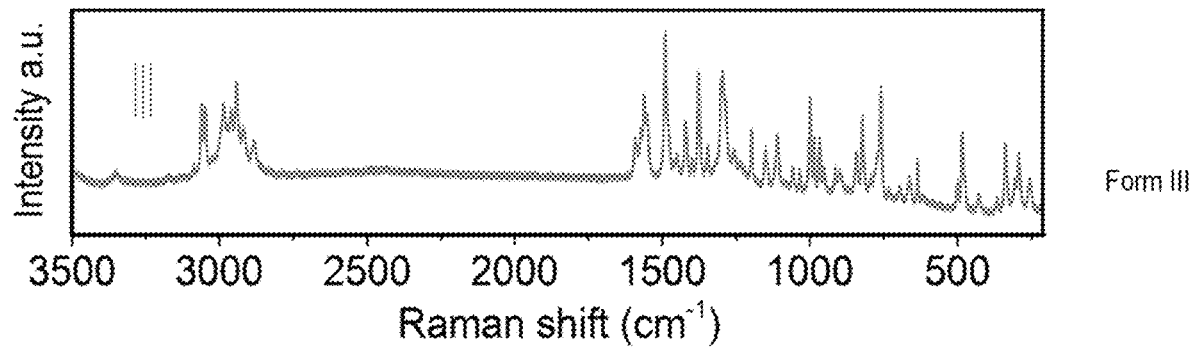
FIG. 8 shows a Raman spectrum of imidacloprid Form III.
Figure 9:
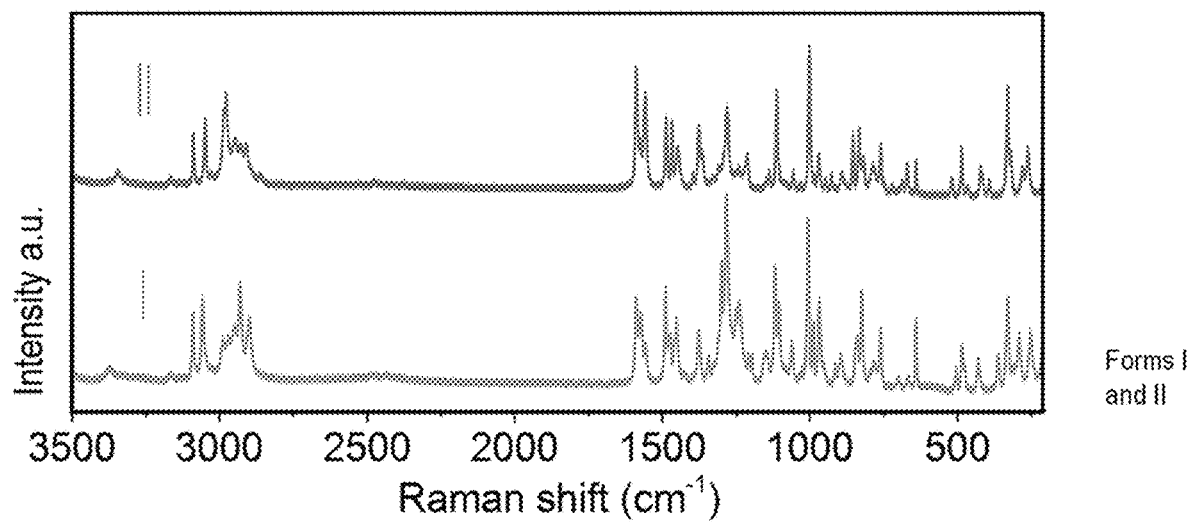
FIG. 9 shows Raman spectra of imidacloprid Forms I and II.
Figure 26:
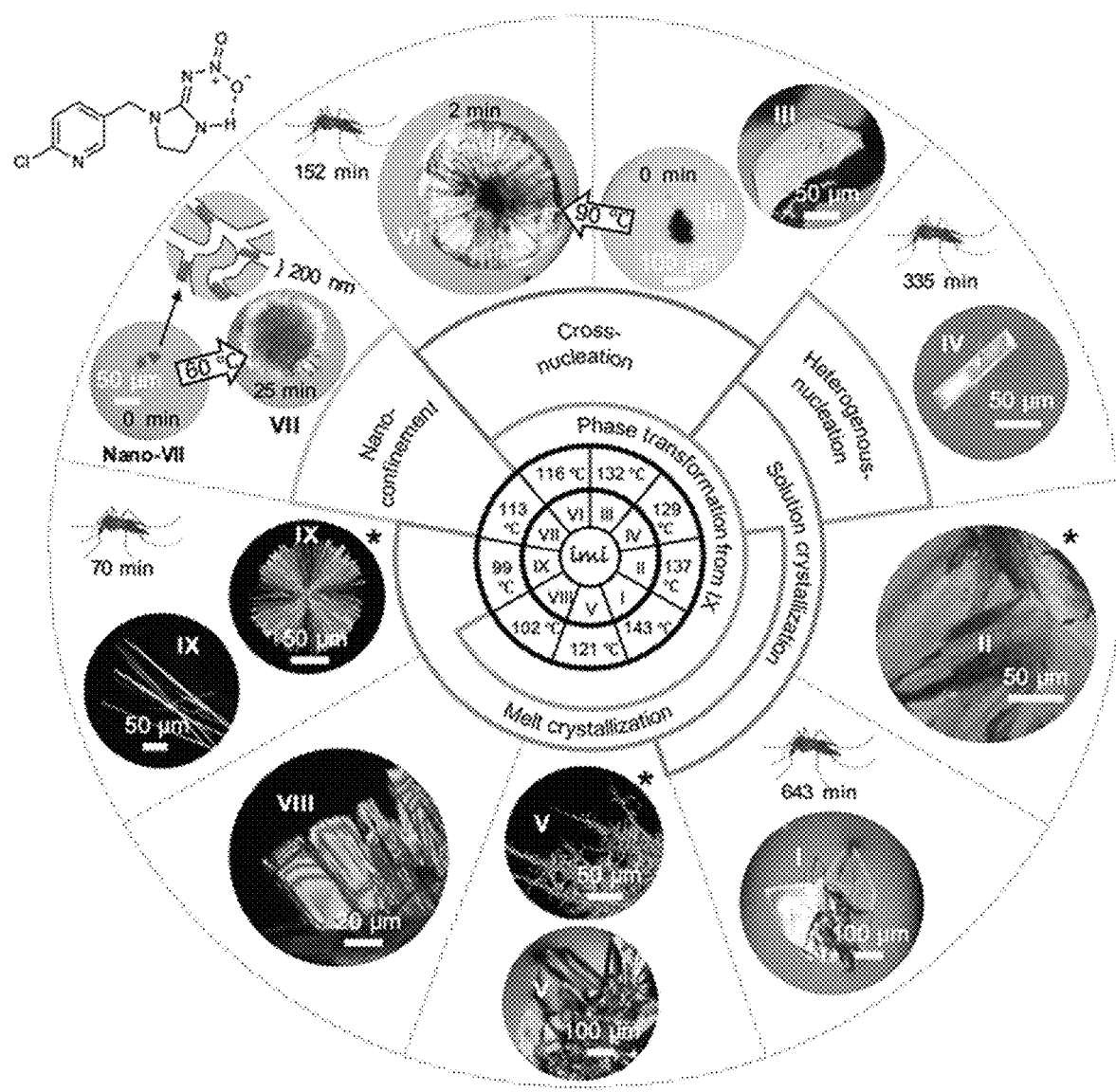
FIG. 26 shows a circle plot depicting the imidacloprid form number, melting points, crystallization methods, microscopic images of crystals, and median knockdown time for female *Aedes* mosquitos for imidacloprid Forms I, II, III, IV, V, VI, VII, VIII, and IX, in accordance with an exemplary embodiment of the present disclosure.
Figure 27A:
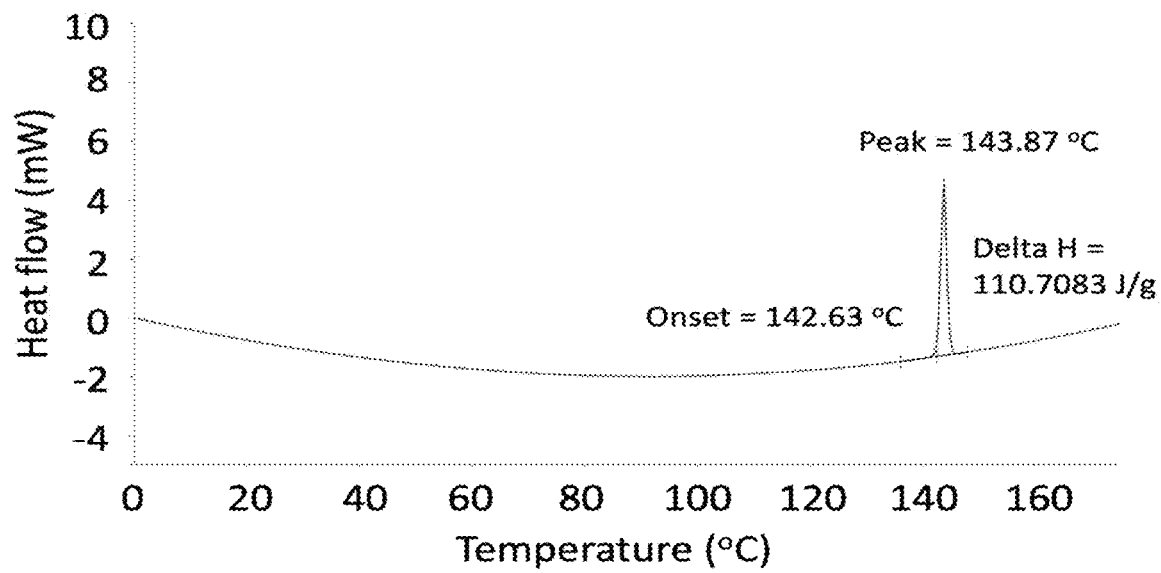
FIGS. 27A and 27B show graphs of DSC in heat flow endo up (mW) v. temperature (° C.).
Figure 27B:
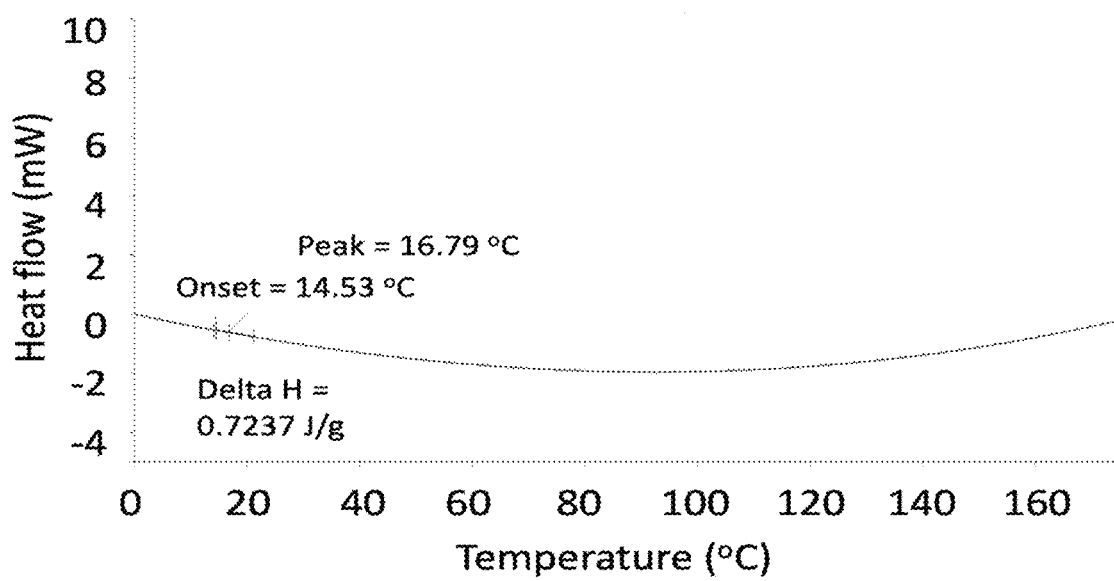
Figure 28A:
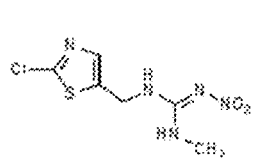
FIGS. 28A-28D show the preparation of imidacloprid Form IV on clothianidin crystals.
Figure 28B:
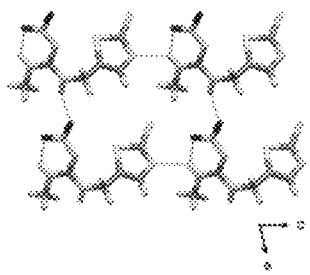
Figure 28C:
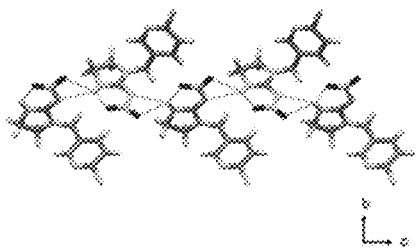
Figure 28D:
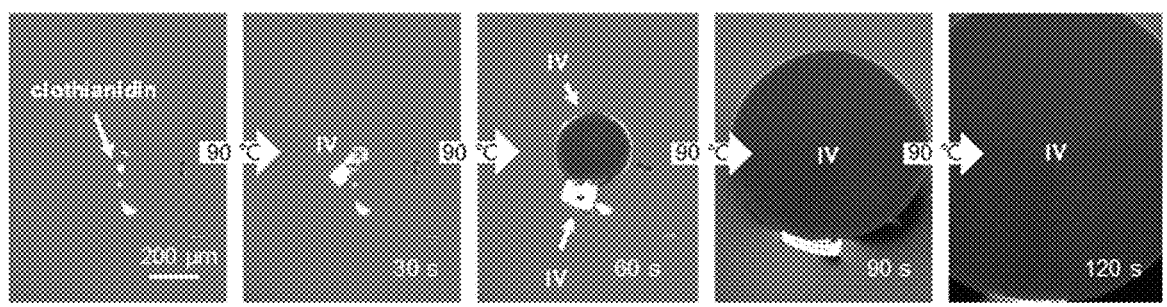

Despite the considerable study and wide use of IMI as a contact insecticide, only two crystal structures have been determined, both measured at ambient temperature and designated as Form I, and Form II. Solution crystallization of IMI from a variety of organic solvents produced Form I, while Form II and a new polymorph, Form IV, can be obtained from acetone and ethanol solutions, respectively. Melt crystallization resulted in the formation of other new polymorphs. Commercial IMI (Sigma-Aldrich) Form I confined between glass slides was melted at ca. 180° C., above its melting point ($T_m$ (Form I)=143° C.) on a microscope hot stage. The melt was subsequently allowed to cool to ambient temperature (25° C.), resulting in the growth of polycrystalline spherulites composed of twisted needles after one week (FIG. 26). Micro-Raman spectroscopy in the N-H stretching region and powder X-ray diffraction (PXRD), confirmed that the spherulites were a new polymorph, herein designated as Form IX (FIG. 2). On rare occasions, chaotic polycrystalline fibrils of a new polymorph, Form V (FIG. 26), and flat crystalline domains of Form II (FIG. 26) also crystallized from the melt. The number of polymorphs were designated according to their melting points measured by a microscope hot stage.

Figure 10A:
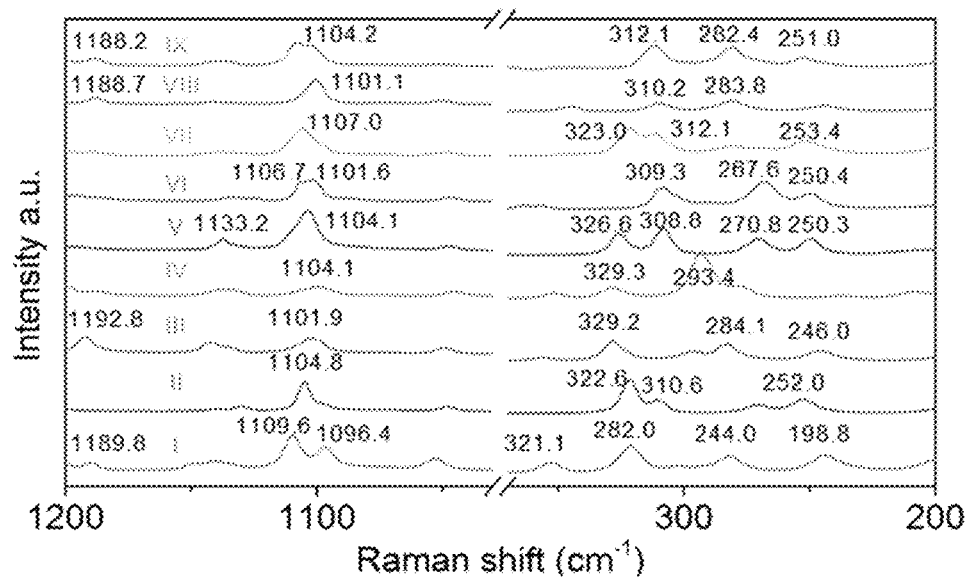
FIGS. 10A and 10B show Raman spectra of imidacloprid Forms I, II, III, IV, V, VI, VII, VIII, and IX.
Figure 10B:
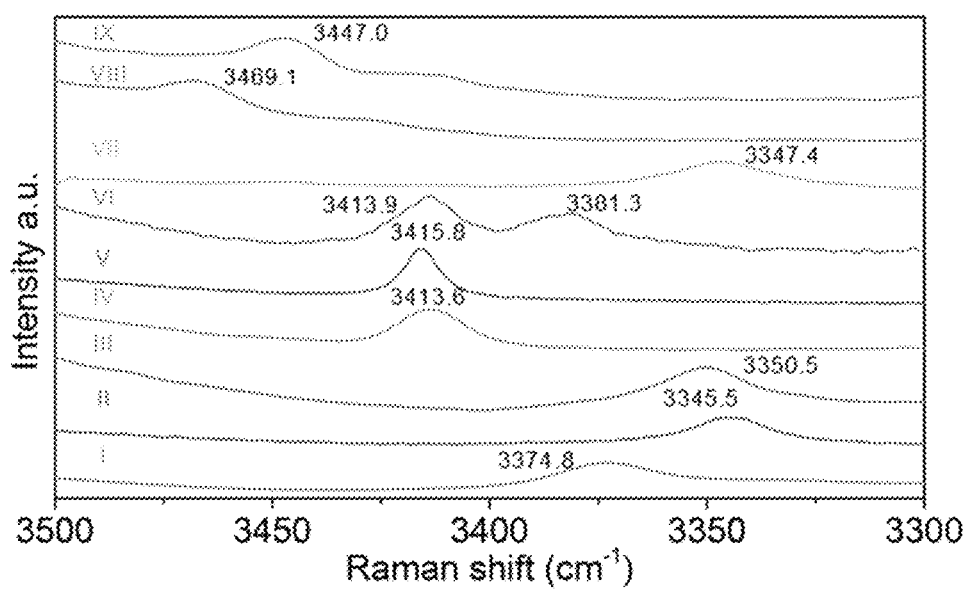
Figure 11:
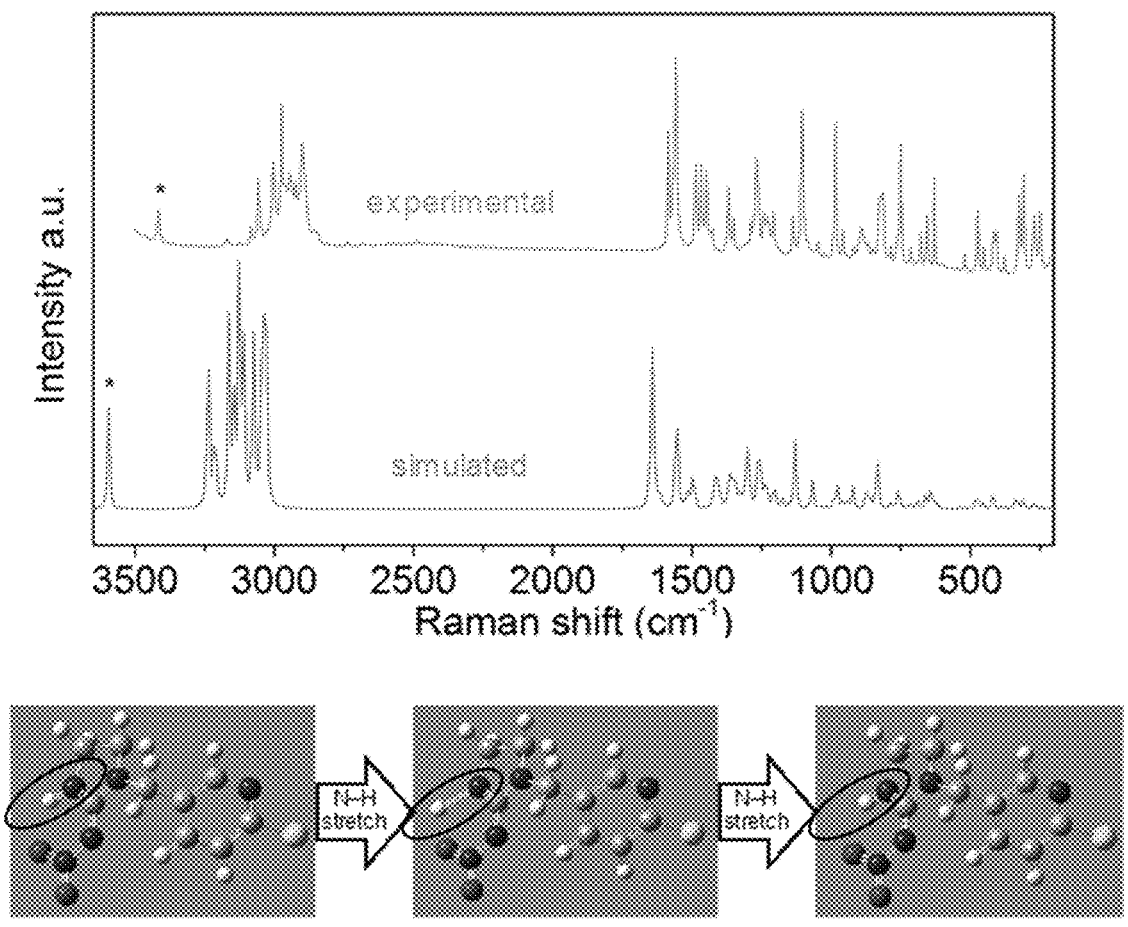
FIG. 11 depicts a simulation and experimental Raman spectra for imidacloprid Form V and an animation showing N—H stretching.
Figure 20:
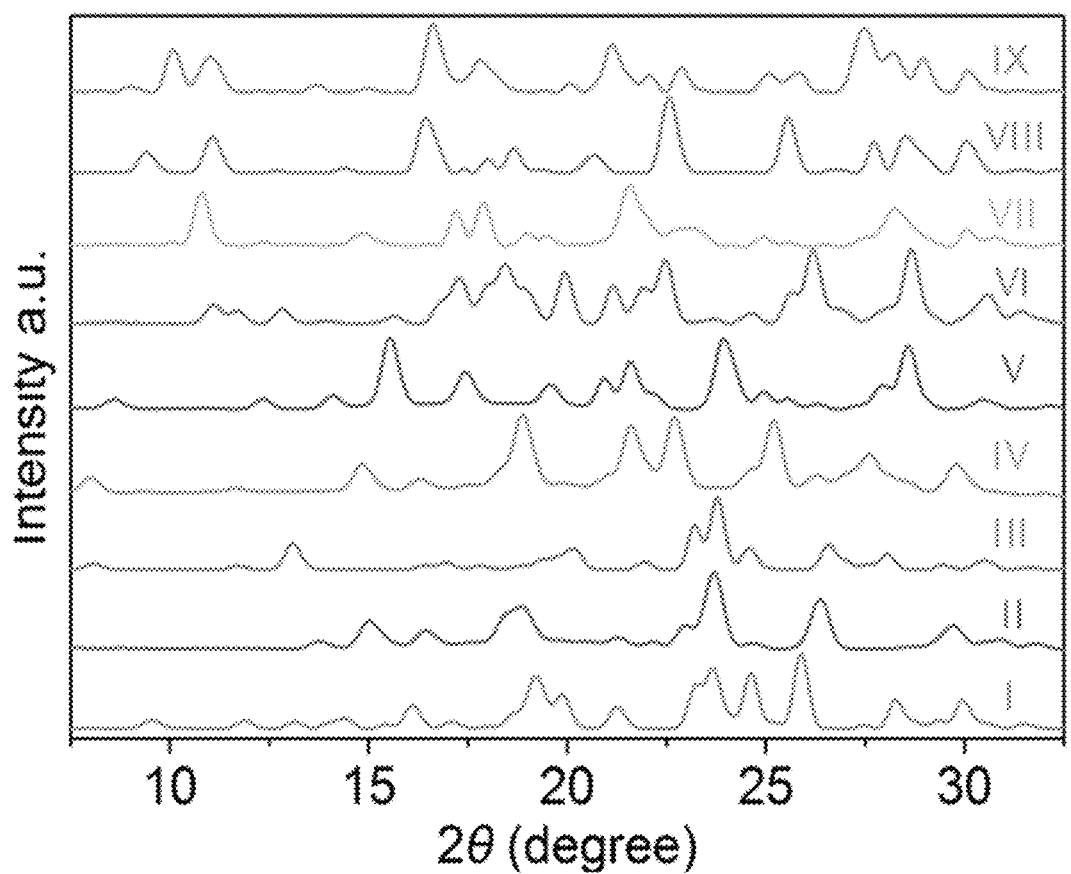
FIG. 20 show powder XRD spectra of imidacloprid Forms I, II, III, IV, V, VI, VII, VIII, and IX.

The crystallization of IMI melt confined between glass slides took up to one month at 25° C. due to its nearby glass transition temperature at $T_g$=15° C. Crystallization could be accelerated, however, by removal of the upper cover slide. Form IX needles emerged from the melt droplets on uncovered glass slides after two days at ambient temperature. Crystals continued to grow for one week. Form IX is stable in open air for up to six months at ambient temperature, although on rare occasions Form IX crystals transformed to other polymorphs after one month. Micro-Raman and PXRD revealed Form IX could transform to Forms I and II, as well as five new polymorphs, herein designated as Forms III, IV, V, VI, and VIII (FIGS. 10A and 10B). Alternatively, Form IV could be prepared through heterogenous nucleation by introducing a seed crystal of commercial clothianidin (Tm=179° C.), another leading neonicotinoid insecticide, to an IMI melt at 60-100° C. Curiously, seeding of melts with Form III crystals at 70-100° C. afforded selective cross-nucleation, of another new polymorph, herein designated as Form VI (FIG. 26) Form III could in turn be obtained by cross-nucleation on Form V at ambient temperature. Nano-confinement of the IMI melt in controlled pore glass beads (CPG, pore size=35, 100, or 200 nm) at ambient temperature produced a new distinct polymorph, Form VII, that was not observed in bulk crystallization. Interestingly, addition of the CPG beads containing Form VII "nanoseeds" to the melt at 60° C. produced needles of Form VII (FIG. 26). Unfortunately, subsequent cross-nucleation of Form II on Form VII, prevented harvesting of Form VII single crystals for X-ray diffraction (FIG. 20). Its powder X-ray diffraction pattern was clearly distinct from the other forms, however. Melt crystallization above 85° C. yield a unique polymorph, herein designated Form VIII (FIG. 26). Single crystals of IMI polymorphs were obtained by crystallization from the melt at various temperatures using their respective crystals as seeds (FIG. 26).

Example 2: Thermodynamic Stability and the Free Energy Ranking

Figure 32A:
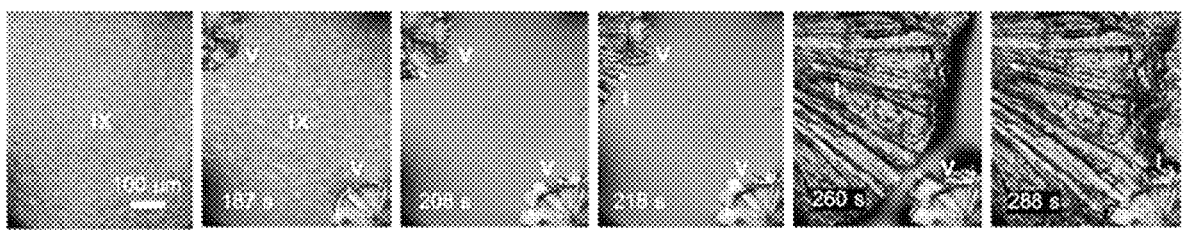
FIGS. 32A-32C show phase transformations among imidacloprid Forms IX to Form I.
Figure 32B:
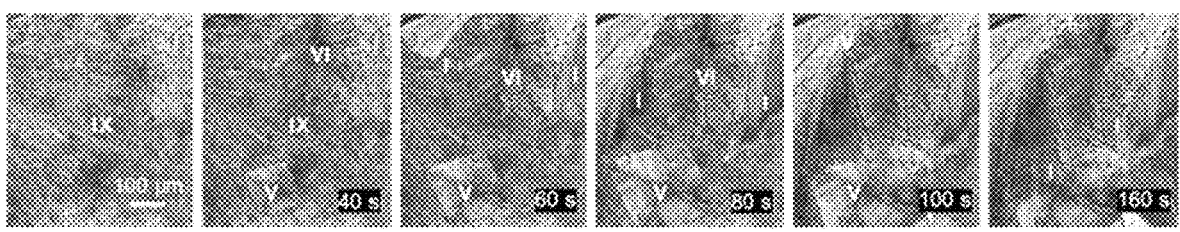
Figure 32C:
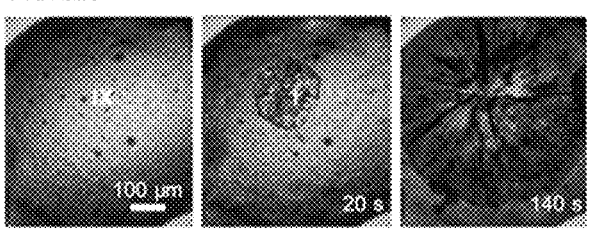
Figure 33A:
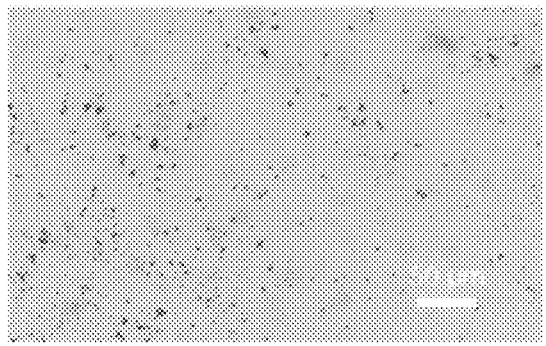
FIGS. 33A-33D show microcrystals of imidacloprid Forms I, IV, VI, and IX used for lethality.
Figure 33B:
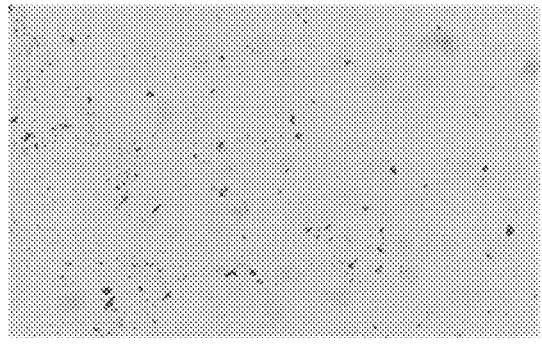
Figure 33C:
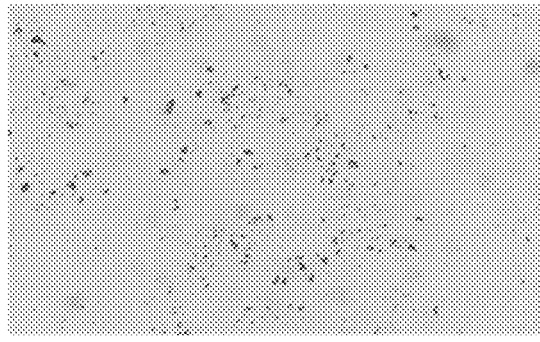
Figure 33D:
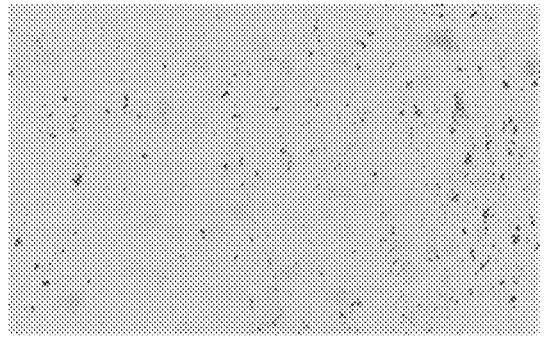

IMI polymorphs exposed in open air at ambient temperature are typically stable for at least 6 months. Although the polymorphic forms were distinguishable by visual inspection (from their interference colors between crossed polarizers and morphologies), their identity and any phase transformations were always corroborated by micro-Raman spectroscopy and PXRD. Form IX held at 95° C. on a microscope hot stage in air transformed to Form V in 3 min, which then converted to Form I at 110° C. in 2 min. Form I also can nucleate directly on the surface of Form IX at T>70° C. Form IX crystals confined between glass slides nucleate Form I, V or VI within Form IX at 80° C. within 1 min. Form IX transforms to Forms II, III or VIII at ambient temperature infrequently, suggesting nucleation is frustrated by a high energy barrier associated with the conformational changes as estimated from gas phase calculations of single molecules. Form VI transforms to III when they were in contact at 110° C. All Forms II-IX can transform to Form I upon heating with a hot stage or in a differential scanning calorimeter (DSC), corroborating that commercial Form I is the most thermodynamically stable crystal form (FIGS. 32A-32C).

Figure 22C:
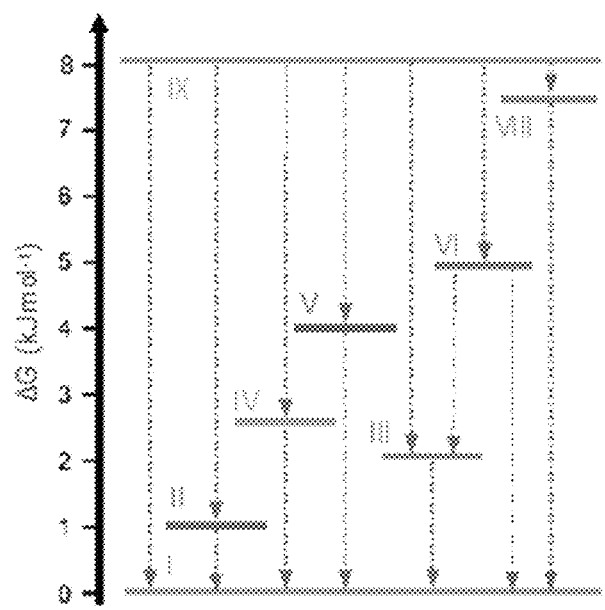
Figure 23A:
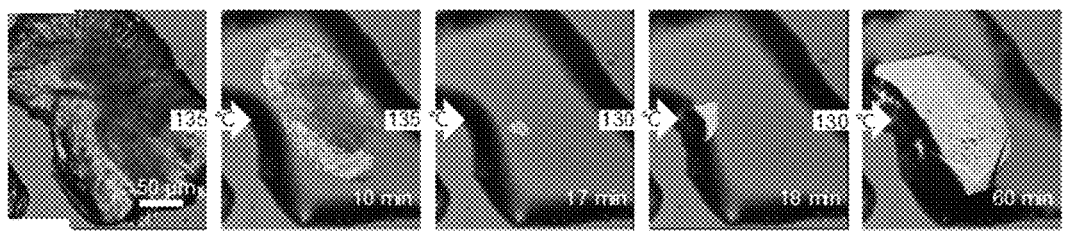
FIGS. 23A-23D show the preparation of imidacloprid single crystals Forms III, IV, V, and IX from melt crystallization, in accordance with an exemplary embodiment of the present disclosure.
Figure 23B:
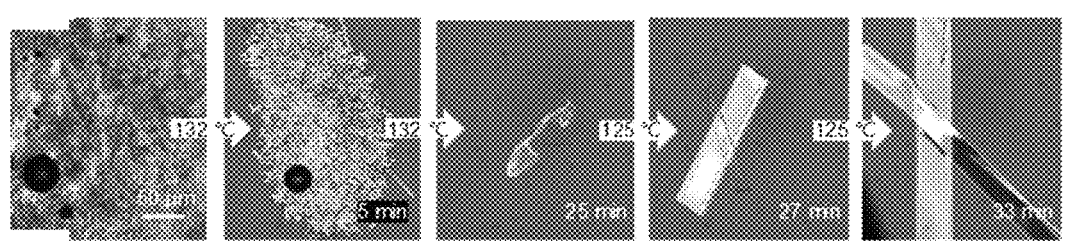
Figure 23C:
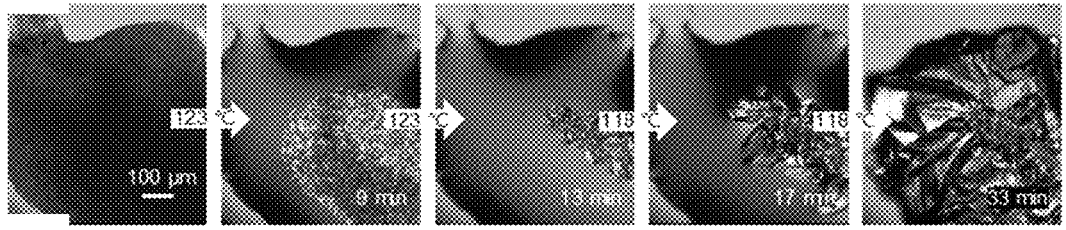
Figure 23D:
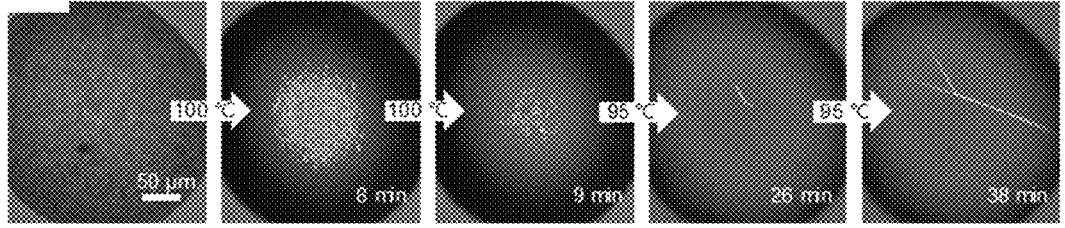

Melting points, Tm, of each polymorph range from 99-143° C., reflecting a wide range of crystal free energies. The free energy ranking discerned from the melting points (I<II<III<IV<V<VI<VII<VIII<IX) correlates exactly with the ranking observed from phase transformations (FIG. 22C). Notably, this order contrasts with the order of the relative energy for the isolated conformers of molecules found in the crystals, demonstrating that the crystal thermodynamic stability rankings depend less on the molecular conformation than on intermolecular interactions in the crystalline forms.

Example 3: Heterogenous Nucleation of IMI Form IV on Clothianidin Crystals

Form IV could be prepared through heterogenous nucleation by introducing a seed crystal of commercial clothianidin (Tm=179° C.), another leading neonicotinoid insecticide, to an IMI melt at 60-100° C. (FIGS. 27A-27D). Heterogeneous nucleation of IMI Form IV was induced by seeding a IMI melt of commercial clothianidin single crystals at 90° C. A polarized light microscope fitted with crossed polarizers (Olympus BX50) and equipped with a digital camera was used to record the crystallization. A microscope hot stage (Mettler FP82HT) was used for temperature control.

Figure 29A:
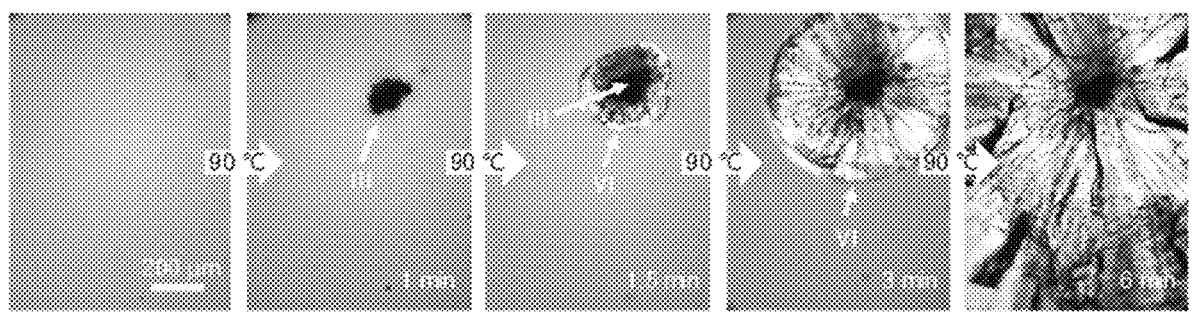
Figure 29B:
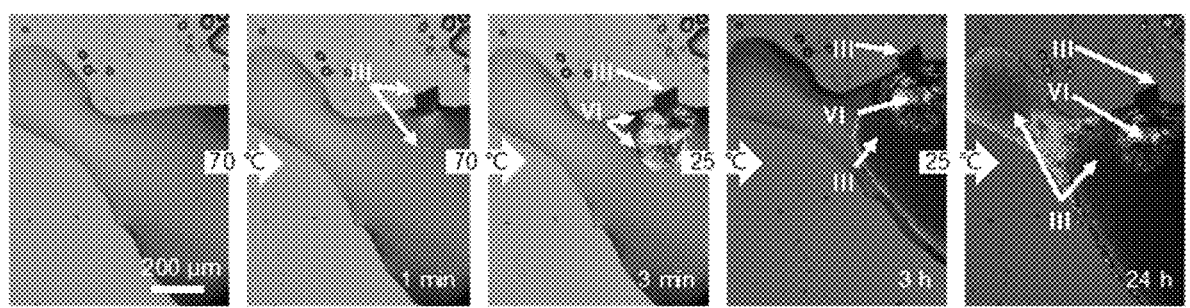
Figure 31A:
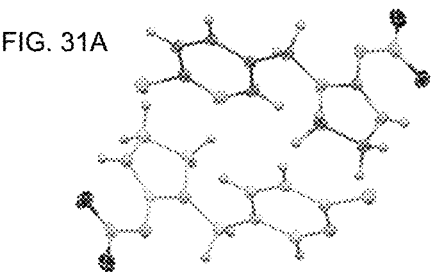
FIGS. 31A-31G show molecular structure of imidacloprid Forms I, III, IV, V, VI, VIII, and IX depicted as ellipsoids in 50% probability.
Figure 31B:
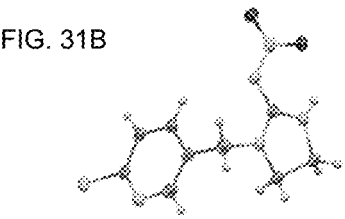
Figure 31C:
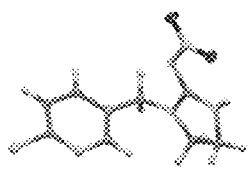
Figure 31D:
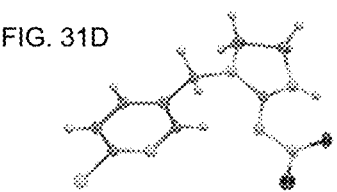
Figure 31E:
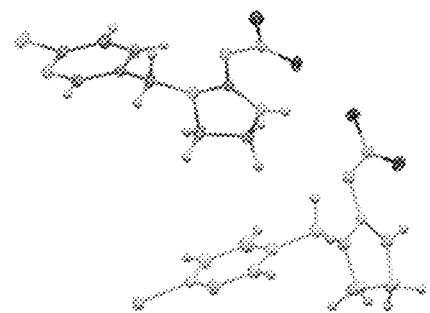
Figure 31F:
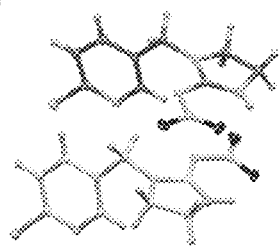
Figure 31G:
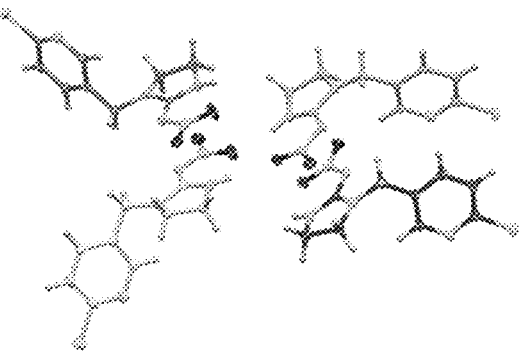

Example 4: Cross-Nucleation Between IMI Forms III and VI by Seeded Nucleation Cross-nucleation between imidacloprid polymorphs are indicated in Table 5 below. Seeding of melts with Form III crystals at 70-100° C. afforded selective cross-nucleation, of Form VI, as shown in FIG. 29A. Cross-nucleation of IMI Form VI was induced by seeding a melt of IMI with single crystals of IMI Form III at 90° C. Form III could in turn be obtained by cross-nucleation on Form V at ambient temperature. FIG. 29B illustrates seeding of a melt of IMI at 70° C. with Form III single crystals afforded the cross-nucleation of Form VI in the first 3 minutes. After the system was allowed to cool to room temperature (25° C.), Form III was obtained by the cross-nucleation on Form VI. A polarized light microscope fitted with crossed polarizers (Olympus BX50) and equipped with a digital camera was used to record the crystallization. A microscope hot stage (Mettler FP82HT) was used for temperature control.

TABLE 5

| Seed crystals[a] | Seeding temperature[b] (° C.) | Growth temperature (° C.) | Resulted polymorph |
| --- | --- | --- | --- |
| Form II | 60 | 60 | Form II |
| Form II | 70 | 70 | Form II |
| Form II | 80 | 80 | Form II |
| Form II | 90 | 90 | Form II |
| Form II | 100 | 100 | Mixture of Forms II and I |
| Form II | 110 | 110 | Mixture of Forms II and I |
| Form III | 50 | 25 | Mixture of Forms III and I |
| Form III | 60 | 60 | Mixture of Forms III and I |
| Form III | 70 | 25 | Form III[c] |
| Form III | 70 | 70 | Form VI |
| Form III | 80 | 80 | Form VI |
| Form III | 90 | 90 | Form VI |
| Form III | 100 | 100 | Form VI |
| Form III | 110 | 110 | Mixture of Forms VI and I |
| Form V | 60 | 60 | Mixture of Forms V and I |
| Form V | 70 | 25 | Mixture of Forms V and I |
| Form V | 70 | 40 | Form V |
| Form V | 70 | 70 | Mixture of Forms V and I |
| Form V | 80 | 80 | Mixture of Forms V and I |
| Form V | 90 | 90 | Mixture of Forms V and I |

TABLE 5-continued

| Seed crystals[a] | Seeding temperature[b] (° C.) | Growth temperature (° C.) | Resulted polymorph |
|---|---|---|---|
| Form VI | 60 | 60 | Form VI |
| Form VI | 70 | 25 | Form III |
| Form VI | 70 | 70 | Form VI |
| Form VI | 80 | 80 | Form VI |
| Form VI | 90 | 90 | Form VI |
| Form VI | 100 | 100 | Form VI |

Example 5: Phase Transformations Among IMI Polymorphs

Transformation of Form IX to Form V at 95° C., which was followed by the melting of Form IX and the transformation of Form V to Form I at 110° C. Transformation of Form IX to Forms V and VI, and finally to Form I at 80° C. The sample was confined between glass slides. c, Transformation of Form IX to Form I at 100° C.

Example 6: Lethality Ranking of IMI Polymorphs

Figure 34A:
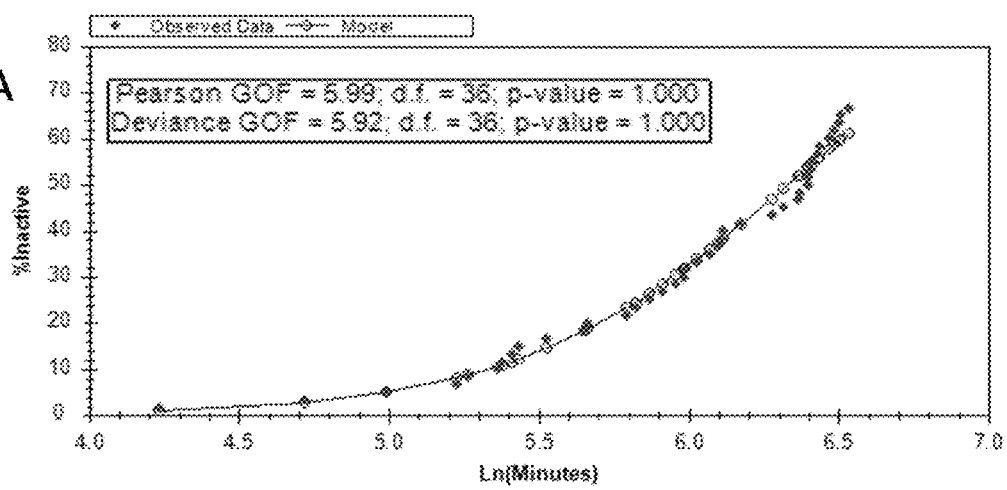
FIGS. 34A-34P show plots of percent inactive v. Ln (minutes) for logistic regression of knock-down time curves for *Drosophila, Aedes, Anopheles*, and *Culex* exposed to microcrystals of imidacloprid Forms I, IV, VI, and IX.
Figure 34B:
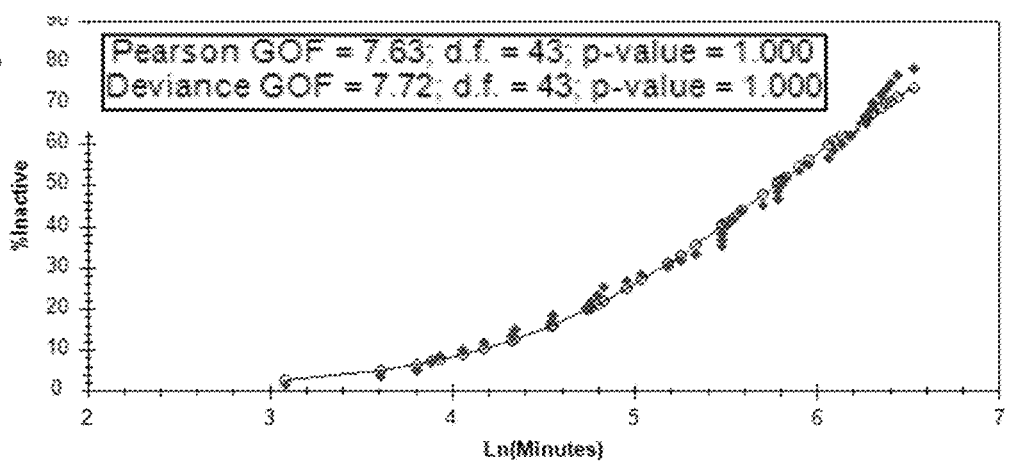
Figure 34C:
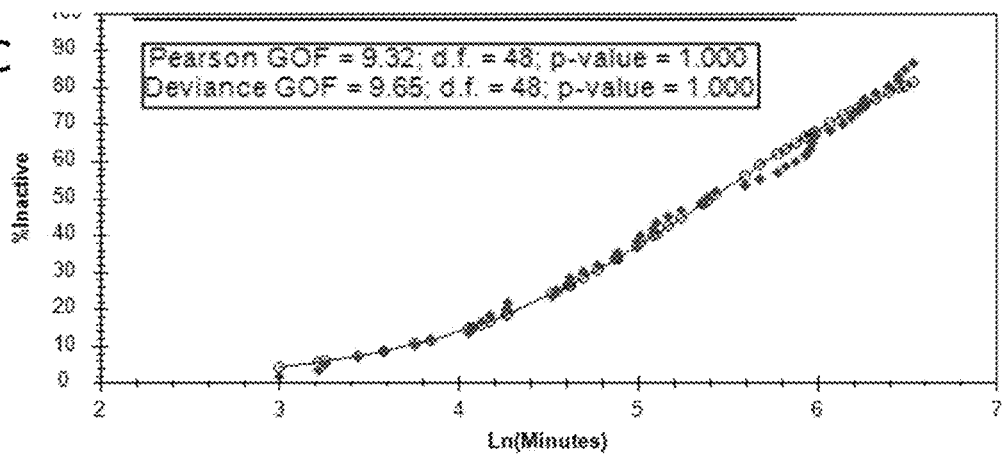
Figure 34D:
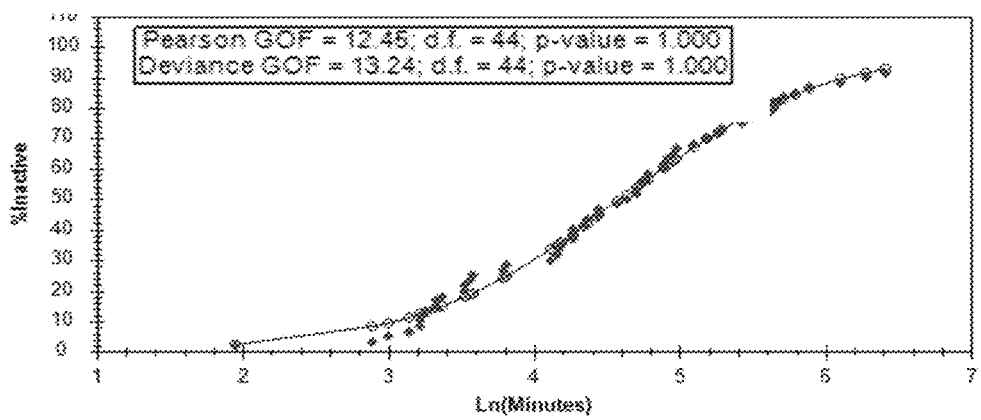
Figure 34E:
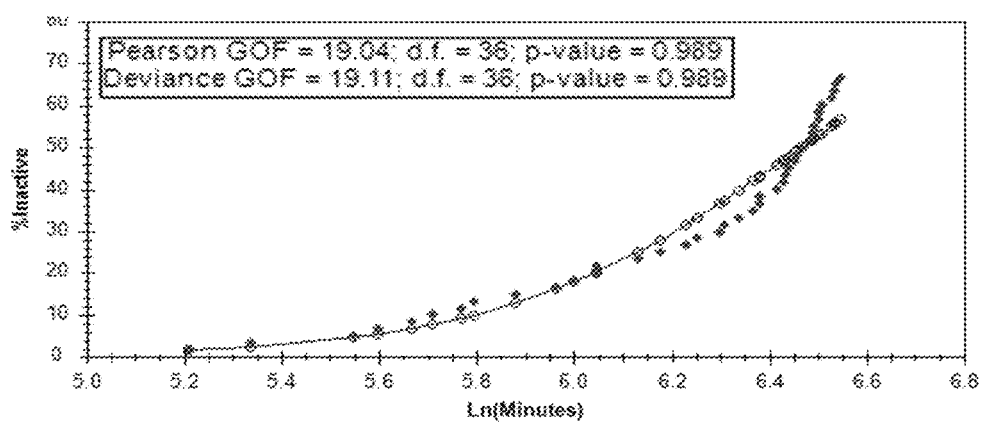
Figure 34F:
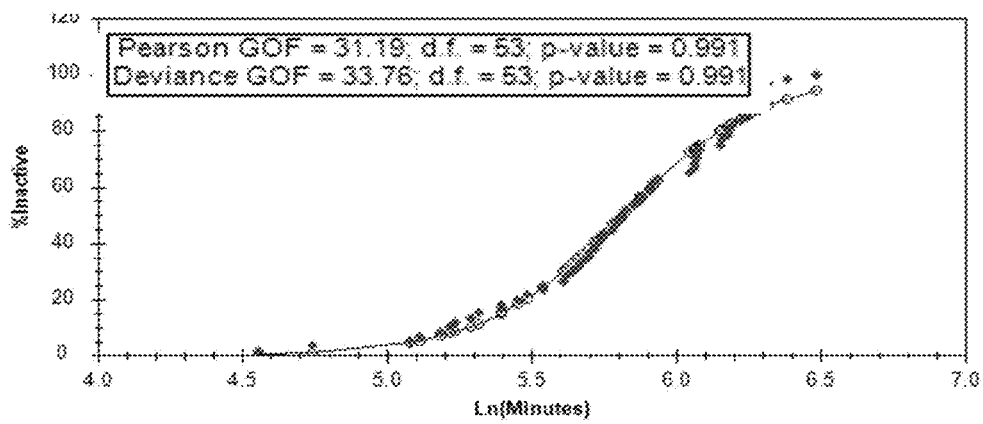
Figure 34G:
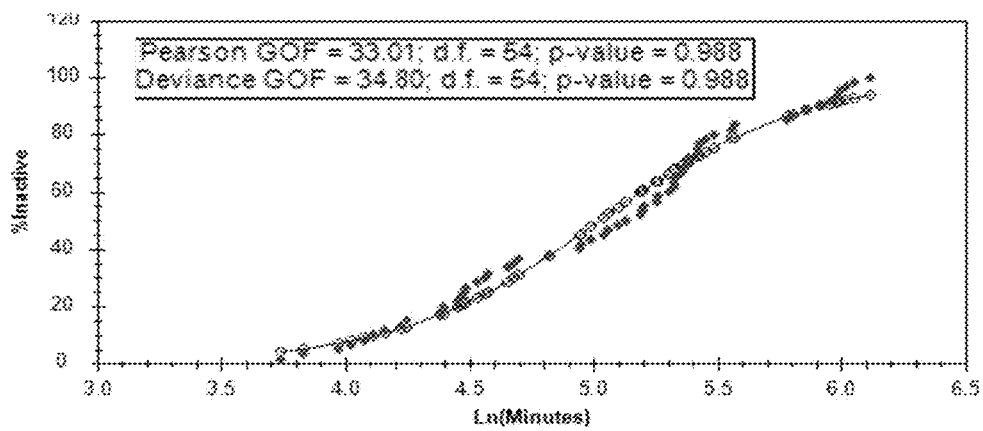
Figure 34H:
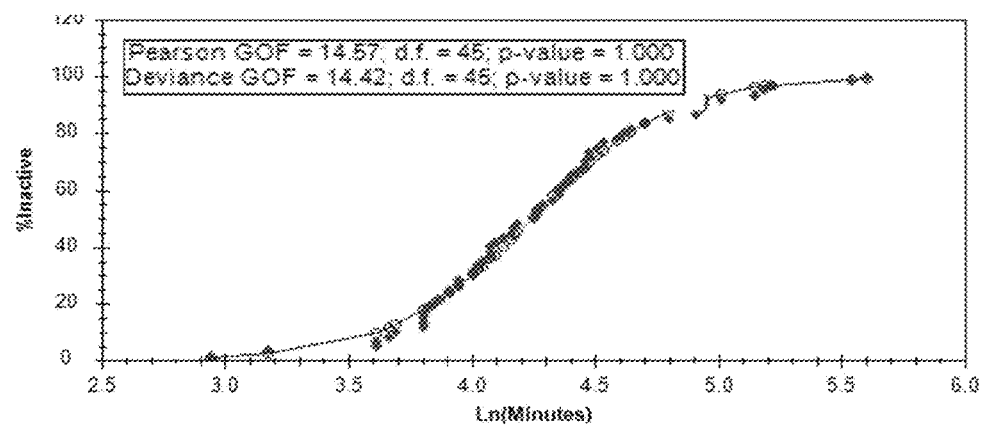
Figure 34I:
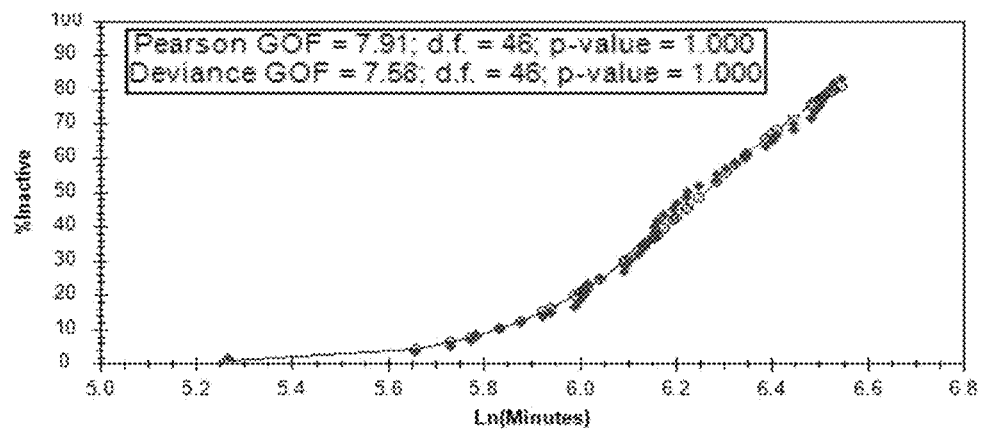
Figure 34J:
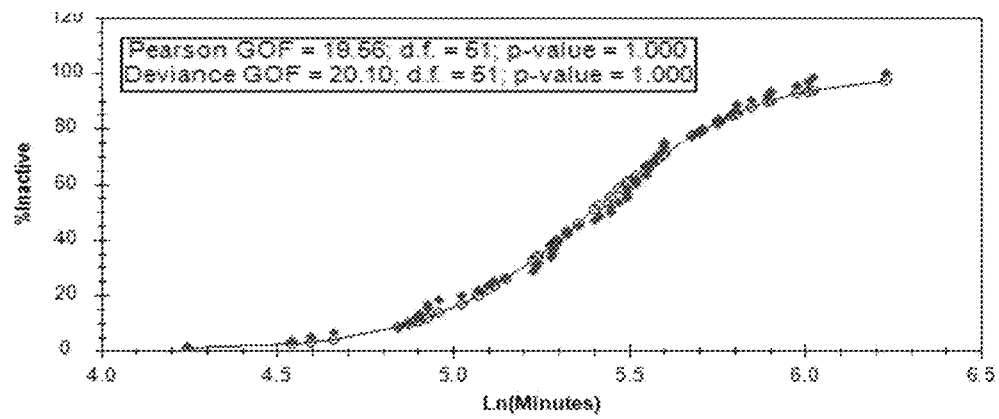
Figure 34K:
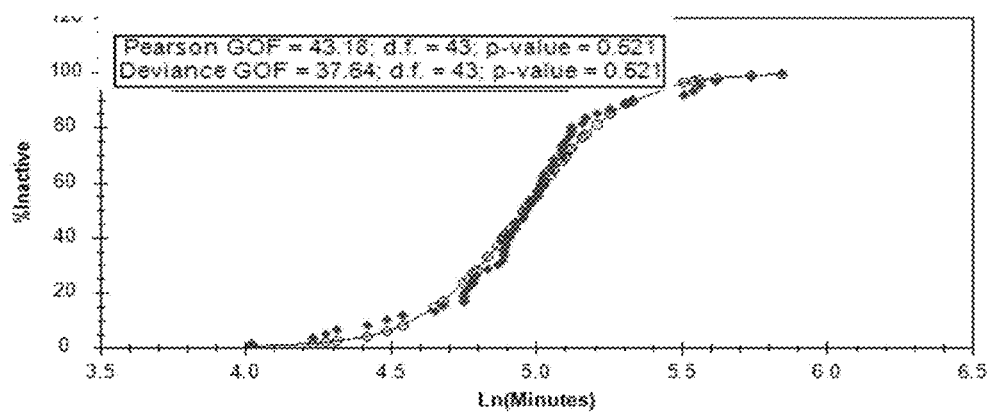
Figure 34L:
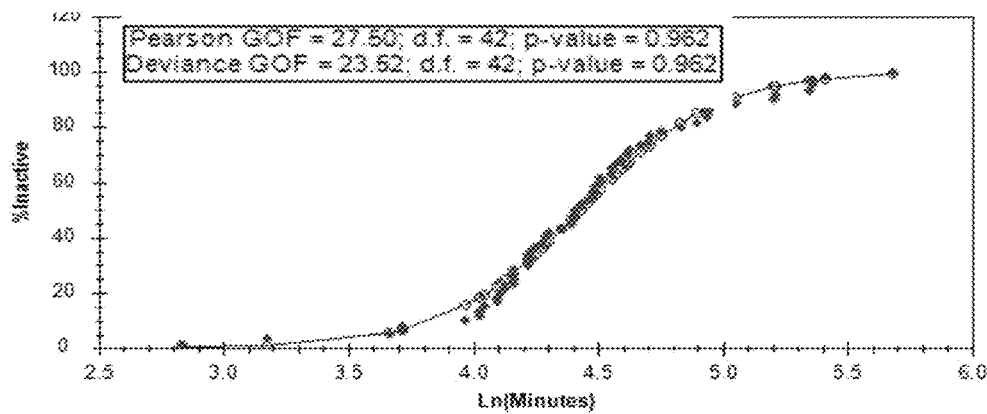
Figure 34M:
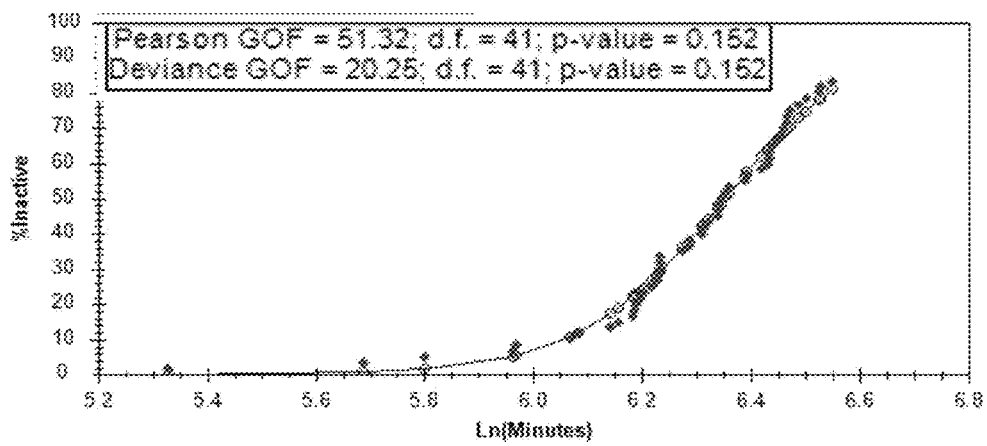
Figure 34N:
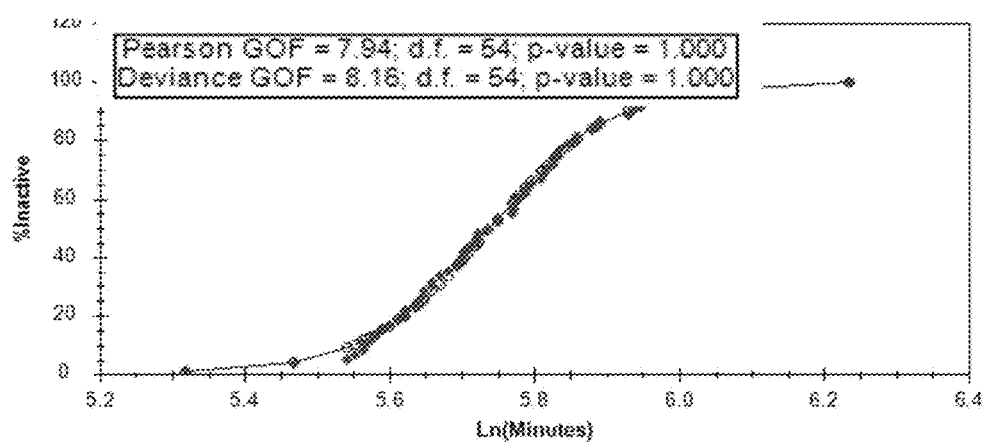
Figure 34O:
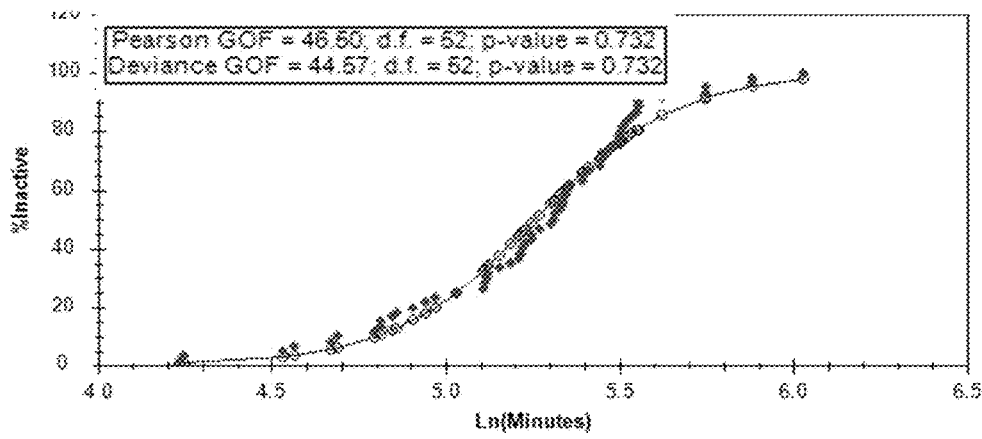
Figure 34P:
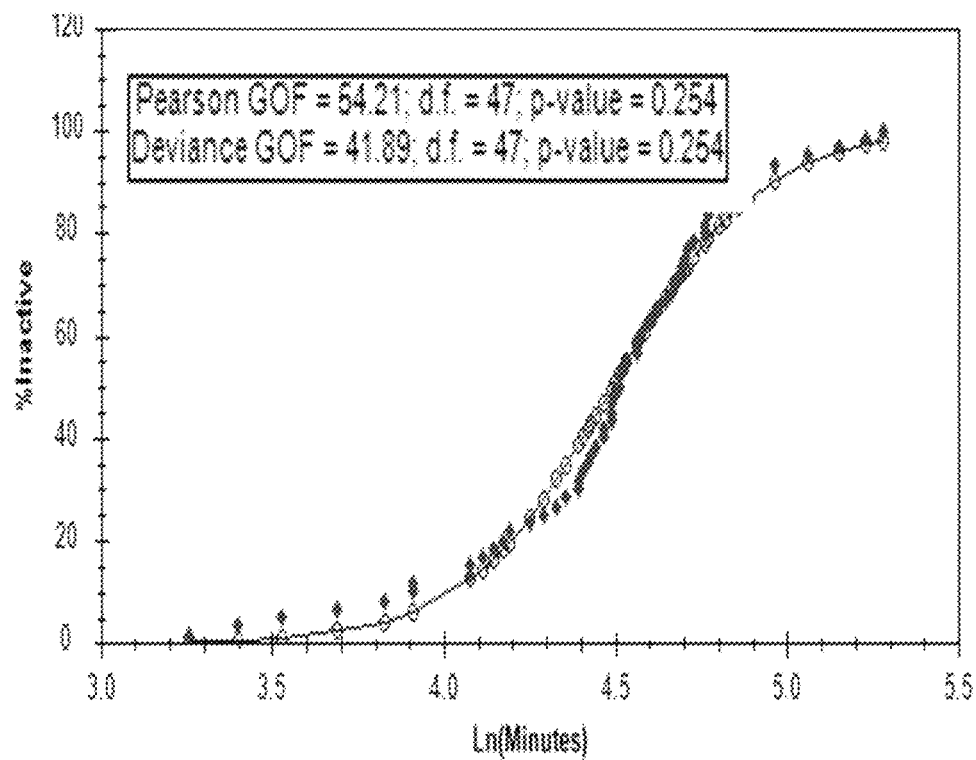
Figure 35A:
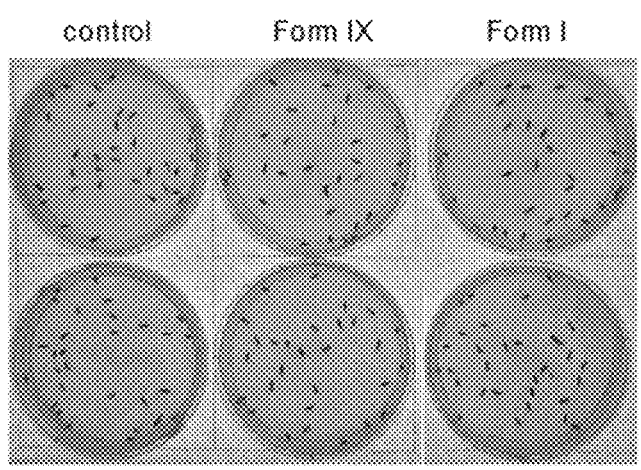
FIGS. 35A-35E show lethality measurements of imidacloprid vapor for *Drosophila* and *Aedes*.
Figure 35B:
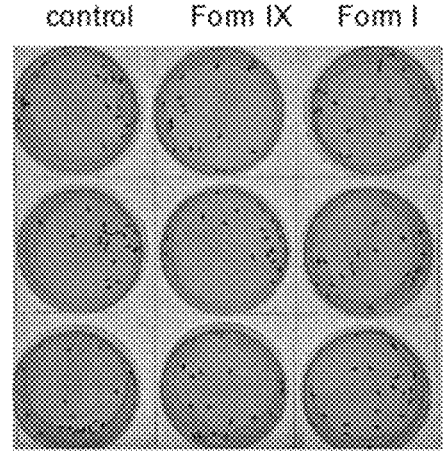
Figure 35C:
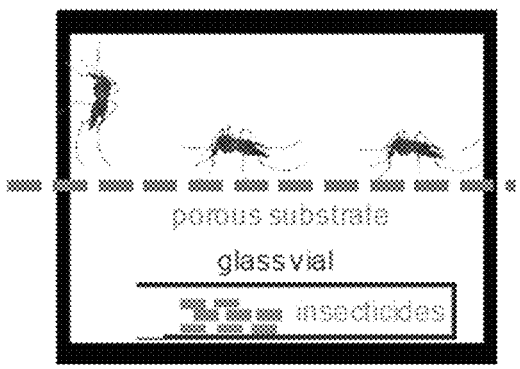
Figure 35D:
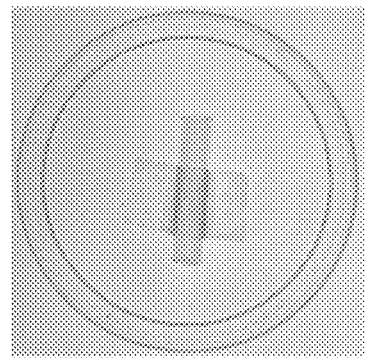
Figure 35E:
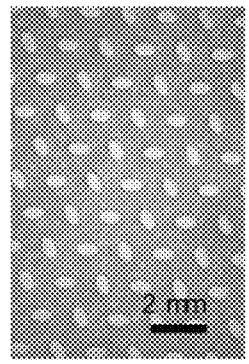

IMI Forms IX, VI, IV were selected for lethality comparison with the commercial Form I, collectively representing a quartet spanning a wide range of free energies. Moreover, these forms were readily prepared from the melt and were kinetically stable against transformations to other polymorphs. Female fruit flies (*Drosophila melanogaster*), a common pest and considered to be a reliable proxy for insecticide development, were exposed to 2.0 mg of nearly monodisperse microcrystals of each IMI polymorph with comparable particle sizes (~10 µm) distributed uniformly on the bottom surfaces of separate 35 mm-diameter polystyrene Petri dishes. Fruit flies exhibited tremors after contacting IMI, followed by prostration, then knockdown. A video camera was used to record the knockdown times—a proxy for lethality—for each insect. $KT_{50}$ values, the times required for 50% of the insects to become immobile and supine, were calculated by logistic regression of knockdown-time curves (FIGS. 34A-34P). Shorter $KT_{50}$ values correspond to greater lethality. The $KT_{50}$ values spanned the range of 562-99 min, decreasing in the order Forms I>IV>VI>IX, as indicated in Table 6 below. Accordingly, Forms IX, VI and IV were 5.7, 2.5 and 1.8 times faster-acting than Form I.

*Aedes* and *Drosophila* exposed to IMI vapor remained viable with no nerve firing symptoms. In contrast, all *Aedes* and *Drosophila* allowed to contact the same amount of IMI microcrystals in petri dishes were knocked down within 10 hours, indicating that effectiveness of IMI vapor is much less than direct contact with *Aedes* and *Drosophila*. Crystalline insecticide was added to an opened glass vial tapped to the bottom of a petri dish, which was subsequently covered with porous polyester substrate. Female *Aedes* and *Drosophila* were sedated with carbon dioxide and were transferred onto the porous substrate. An inverted petri dish was then placed over the polyester substrate to seal the assembly. The motion of the *Aedes* and *Drosophila* was recorded with a video camera. An opened glass vial containing 2.0 mg IMI microcrystals was tapped to the bottom of the petri dish (FIGS. 35A-35E).

*Aedes* and *Drosophila* exposed to IMI vapor remained viable with no nerve firing symptoms after 12 hours (FIGS. 34A-34P), corroborating the reported low vapor pressure and inactive vapor phase of IMI. Therefore, the different lethalities of IMI polymorphs can be attributed to the rate of uptake of molecules from crystal surfaces upon contact of the insect tarsi. The remarkable decrease in knockdown times of metastable polymorphs indicates that the rate-limiting step in the contact exposure of IMI is the detachment of molecules from crystal surfaces, consistent with the correlation of the $KT_{50}$ values with the crystal free energies Current gains in infectious disease control are greatly threatened by the widespread resistance to conventional insecticides, such as pyrethroids. The recent outbreaks and spread of Zika virus, and yellow fever transmitted by *Aedes* mosquitoes also post new challenges to public health. Meanwhile, mosquito metabolism and population size will increase sharply in many regions as the planet continues to warm requiring more effective vector control. Fast action is an important consideration for public health insecticides, as vectors need to be quickly incapacitated to interrupt disease transmission. New polymorphs significantly increase the contact activity of IMI, minimizing its knockdown speed as a limiting factor compared to pyrethroids.1 Moreover, the increased uptake speeds of IMI molecules from metastable polymorphs may quickly saturate over-expressed detoxification enzymes, therefore ensuring the lethal dose still reach the target site to circumvent nascent insecticide resistance.

TABLE 6

| Insect | IMI polymorph | $KT_{50}$ (95% CI) (min) | Slope ± SE | Intercept ± SE |
|---|---|---|---|---|
| *Drosophila* | Form I | 562 (536-589) | 2.21 ± 0.13 | −13.98 ± 0.79 |
| *Drosophila* | Form IV | 321 (302-343) | 1.37 ± 0.06 | −7.89 ± 0.36 |
| *Drosophila* | Form VI | 223 (210-238) | 1.30 ± 0.05 | −7.05 ± 0.28 |
| *Drosophila* | Form IX | 99 (93-105) | 1.42 ± 0.05 | −6.52 ± 0.25 |
| *Aedes* | Form I | 643 (621-664) | 3.28 ± 0.20 | −21.23 ± 1.28 |
| *Aedes* | Form IV | 335 (329-342) | 4.12 ± 0.15 | −23.98 ± 0.85 |
| *Aedes* | Form VI | 152 (147-157) | 2.46 ± 0.08 | −12.34 ± 0.42 |
| *Aedes* | Form IX | 70 (68-71) | 3.51 ± 0.13 | −14.90 ± 0.54 |
| *Anopheles* | Form I | 524 (515-534) | 5.12 ± 0.22 | −31.98 ± 1.37 |
| *Anopheles* | Form IV | 220 (216-224) | 4.30 ± 0.15 | −23.19 ± 0.84 |
| *Anopheles* | Form VI | 143 (141-144) | 5.81 ± 0.23 | −28.82 ± 1.16 |
| *Anopheles* | Form IX | 84 (82-86) | 3.68 ± 1.34 | −16.30 ± 0.61 |
| *Culex* | Form I | 573 (568-581) | 7.43 ± 0.34 | −47.20 ± 2.18 |
| *Culex* | Form IV | 311 (309-313) | 11.68 ± 0.41 | −67.03 ± 2.37 |
| *Culex* | Form VI | 192 (189-195) | 4.82 ± 0.18 | −25.32 ± 0.95 |
| *Culex* | Form IX | 89 (88-91) | 4.70 ± 0.18 | −21.09 ± 0.82 |

Example 7: Crystal Data for IMI Polymorphs

Crystallographic data of imidacloprid Forms I, III, IV, V, VI, VII, and IX are as indicated in Table 7 below.

TABLE 7

|  | Form I | Form III | Form IV | Form V | Form VI | Form VIII | Form IX |
|---|---|---|---|---|---|---|---|
| Formula | $C_9H_{10}ClN_5O_2$ | $C_9H_{10}ClN_5O_2$ | $C_9H_{10}ClN_5O_2$ | $C_9H_{10}ClN_5O_2$ | $C_9H_{10}ClN_5O_2$ | $C_9H_{10}ClN_5O_2$ | $C_9H_{10}ClN_5O_2$ |
| Formula weight | 255.67 | 255.67 | 255.67 | 255.67 | 255.67 | 255.67 | 255.67 |
| Crystal system | Monoclinic | Monoclinic | Monoclinic | Monoclinic | Monoclinic | Triclinic | Triclinic |
| Space group (no.) | $P2_1/n$ (14) | $P2_1/c$ (14) | $P2_1/c$ (14) | $P2_1/c$ (14) | $P2_1/c$ (14) | P-1 (2) | P-1 (2) |
| a (Å) | 12.378 (2) | 11.3264 (5) | 4.8498 (5) | 10.050 (3) | 10.7171 (12) | 6.4420 (4) | 6.4692 (4) |
| b (Å) | 9.5340 (17) | 10.4652 (5) | 21.120 (2) | 9.961 (3) | 13.8254 (16) | 9.2449 (5) | 17.2049 (10) |
| c (Å) | 18.880 (3) | 9.8634 (5) | 10.5617 (10) | 10.830 (4) | 15.2387 (17) | 18.5409 (11) | 21.3255 (12) |
| α (°) | 90 | 90 | 90 | 90 | 90 | 82.361 (2) | 66.5670 (19) |
| β (°) | 102.648 (3) | 112.1890 (10) | 98.2015 (14) | 96.882 (4) | 101.216 (2) | 84.415 (2) | 83.849 (2) |
| γ (°) | 90 | 90 | 90 | 90 | 90 | 80.369 (2) | 82.909 (2) |
| V (Å$^3$) | 2174.1 (7) | 1082.56 (9) | 1070.72 (18) | 1076.4 (6) | 2214.8 (4) | 1075.80 (11) | 2156.8 (2) |
| Z | 8 | 4 | 4 | 4 | 8 | 4 | 8 |
| $D_c$ (g cm$^{-3}$) | 1.562 | 1.569 | 1.586 | 1.578 | 1.534 | 1.579 | 1.575 |
| μ (mm$^{-1}$) | 0.350 | 0.351 | 0.355 | 0.353 | 0.343 | 0.354 | 0.353 |
| F(000) | 1056 | 528 | 528 | 528 | 1056 | 528 | 1056 |
| Total reflections | 33299 | 16327 | 16210 | 12200 | 32772 | 29973 | 68216 |
| Unique reflections | 5428 | 2684 | 2666 | 2717 | 5485 | 5331 | 8196 |
| $R_{int}$ | 0.0355 | 0.0264 | 0.0424 | 0.0768 | 0.0333 | 0.0517 | 0.0544 |
| GOF | 1.045 | 1.060 | 1.077 | 1.030 | 1.039 | 1.074 | 1.181 |
| $R_1{}^a$ [I > 2σ(I)] | 0.0368 | 0.0327 | 0.0373 | 0.0546 | 0.0349 | 0.0351 | 0.0603 |
| $wR_2{}^b$ (all data) | 0.1034 | 0.0853 | 0.0930 | 0.1454 | 0.0942 | 0.0754 | 0.1086 |

$^a R_1 = \Sigma||F_o| - |F_c||/\Sigma|F_o|;$
$^b wR_2 = \{\Sigma[w(F_o{}^2 - F_c{}^2)^2]/\Sigma[w(F_o{}^2)^2]\}^{1/2}$ Seven (Forms III-IX) novel forms of the world's leading insecticide, imidacloprid (IMI), have been surprisingly discovered. Six (Forms III-VI, VIII, and IX) have been reduced to X-ray structures. The relative stabilities of the complete set of nine polymorphs (Forms I-IX) have been established from melting points and solid state phase transformations. Without wishing to be bound by theory, it has been hypothesized that the lethality of polymorphs would be governed by their thermodynamic instability as the most metastable molecules will deliver molecules at presumably greater rates in tarsal contact with microcrystals. Four novel forms have been tested against *Drosophila*, as well as *Anopheles, Aedes*, and *Culex* mosquitoes. As described above, the lethalities increased in the following order for a range of polymorphs assayed: I (143° C.)>IV (129° C.)>VI (116° C.)>IX (99° C.) (melting points are given parenthetically). Form IX is easy to prepare and microcrystals are stable in air for at least six months. Therefore, Form IX, as well as other forms described herein, is suitable in formulations for infectious disease control to improve the activity of IMI in smaller application, reducing cost and planetary exposure.

REFERENCES

1. United Nations sustainable development goals. https://sustainabledevelopment.un.org/topics/sustainabledevelopmentgoals.
2. McBeath, J. A brief history and future potential of neonicotinoid use in public health. *Int. Pest Control* 59, 214-215 (2017)
3. Oxborough, R. M. et al. Susceptibility testing of *Anopheles malaria* vector with the neonicotinoid insecticide, clothianidin; results from 16 African countries, in preparation for indoor residual spraying with new insecticide formulations, *Malaria J.* 18, 264 (2019).
4. Kupferschmidt, K. Pick your poison. Science 354, 171-173 (2016).
5. Georghiou, G. P. & Mellon, R. B. Pesticide resistance in time and space. In *Pest Resistance to Pesticides,* 1-46 (Springer, Boston, 1983).
6. World Health Organization. Prequalified lists: vector control products. (WHO, Geneva, 2020).
7. World Health Organization. *A Global Brief on Vector-Borne Diseases* (WHO, Geneva, 2014).
8. WHO Prequalification Team. Cielo ULV adulticide space spray. (WHO, Geneva, 2019).
9. Pridgeon, J. W. et al. Susceptibility of *Aedes aegypti, Culex quinquefasciatus* Say, and *Anopheles quadrimaculatus* to 19 pesticides with different modes of action. *J Med Entomol* 45, 82-87 (2008).
10. Yamamoto, I. & Casida, J. E. *Nicotinoid Insecticides and the Nicotinic Acetylcholine Receptor* (Springer-Verlag, Tokyo, 1999).
11. Sheets, L. P. Imidacloprid a neonicotinoid insecticide. In *Hayes' Handbook of Pesticide Toxicology,* 3rd ed., ch 95, 2055-2064 (Elsevier Academic Press, San Diego, 2010).
12. Simon-Delso, N. et al. Systemic insecticides (neonicotinoids and fipronil): trends, uses, mode of action and metabolites. *Environ. Sci. Pollut. Res.* 22, 5-34 (2015).
13. Buchholz, A. & Nauen, R. Translocation and translaminar bioavailability of two neonicotinoid insecticides after foliar application. *Pest Manage. Sci.* 58, 10-16 (2002).
14. Weichel, L. & Nauen, R. Uptake, translocation and bioavailability of imidacloprid in several hop varieties. *Pest Manag. Sci.* 60, 440-446 (2003).

15. Goulson, D. Review: an overview of the environmental risks posed by neonicotinoid insecticides. *J. Appl. Ecol.* 50, 977-987 (2013).
16. Morrissey, C. A. et al. Neonicotinoid contamination of global surface waters and associated risk to aquatic invertebrates: a review. *Environ. Int.* 74, 291-303 (2015).
17. Hallmann, C. A. Foppen, R. P. B. van Turnhout, C. A. M. de Kroon, H. & Jongejans, E. Declines in insectivorous birds are associated with high neonicotinoid concentrations. *Nature* 511, 341-343 (2014).
18. Eng, M. Stutchbury, B. Morrissey, C. A neonicotinoid insecticide reduces fueling and delays migration in songbirds. *Science* 365, 1177-1180 (2019).
19. van Klink, R. et al. Meta-analysis reveals declines in terrestrial but increases in freshwater insect abundances. *Science* 368, 417-420 (2020).
20. Basset, Y. & Lamarre, G. P. Toward a world that values insects. *Science* 364, 1230-1231 (2019).
21. Whitehorn, P. R. O'Connor, S. Wackers, F. L. & Goulson, D. Neonicotinoid pesticide reduces bumble bee colony growth and queen production. *Science* 336, 351-352 (2012).
22. Kessler, S. C. et al. Bees prefer foods containing neonicotinoid pesticides. *Nature*, 521, 74-76 (2015).
23. Stanley, D. A. et al. Neonicotinoid pesticide exposure impairs crop pollination services provided by bumblebees. *Nature* 528, 548-550 (2015).
24. Crall, J. D. et al. Neonicotinoid exposure disrupts bumblebee nest behavior, social networks, and thermoregulation. *Science* 362, 683-686 (2018).
25. Sanchez-Bayo, F., Goulson, D., Pennacchio, F., Nazzi, F., Goka, K., Desneux, N. Are bee diseases linked to pesticideinsecticides?—a brief review. Environ. Int. 89, 7-11 (2016).
26. Biodiversity Act, 2016. Law no. 2016-1087, 8 August 2016, For the return of biodiversity, nature, and countryside. https://www.legifrance.gouv.fr/eli/loi/2016/8/8/2016-1087/jo/texte.
27. Pretty, J. & Bharucha, Z. P. Integrated Pest Management for sustainable intensification of agriculture in Asia and Africa. *Insects* 6, 152-182 (2015).
28. Dzul-Manzanilla, F. et al. Field efficacy trials of aerial ultra-low-volume application of insecticides against caged *Aedes aegypti* in Mexico. *J. Am. Mosquito. Contr.* 35, 140-146 (2019).
29. Yang, J. et al. DDT polymorphism and the lethality of crystal forms. *Angew. Chem. Int. Ed.* 56, 10165-10169 (2017).
30. Yang, J. et al. Inverse correlation between lethality and thermodynamic stability of contact insecticide polymorphs. *Cryst. Growth Des.* 19, 1839-1844 (2019).
31. Zhu, X. et al. Manipulating solid forms of contact insecticides for infectious disease prevention. *J. Am. Chem. Soc.* 141, 16858-16864 (2019).
32. Yang, J. et al. A deltamethrin crystal polymorph for more effective malaria control. *Proc. Natl. Acad. Sci. U.S.A.* 117, 26633-26638 (2020).
33. Zhao, J. Wang, M. Dong, B. Feng, Q. & Xu, C. Monitoring the polymorphic transformation of imidacloprid using in situ FBRM and PVM. *Org. Proc. Res. Dev.* 17, 375-381 (2013).
34. Kagabu, S. & Matsuno, H. Chloronicotinyl insecticides. 8. Crystal and molecular structures of imidacloprid and analogous compounds. *J. Agric. Food Chem.* 45, 276-281 (1997).
35. Chopra, D. Mohan, T. P. Rao, K. S. & Row, T. N. G. (2E)-1-[(6-Chloropyridin-3-yl)methyl]-N-nitro-imidazolidin-2-imine (imidachloprid). *Acta Crystallogr. Sect. E: Struct. Rep. Online* 60, o2415-o2417 (2004).
36. Zhu, Q. et al. Resorcinol crystallization from the melt: A new ambient phase, and new "riddles". *J. Am. Chem. Soc.* 138, 4881-4889 (2016).
37. Shtukenberg, A. G. et al. Powder diffraction and crystal structure prediction reveal four new coumarin polymorphs. *Chem. Sci.* 8, 4926-4940 (2017).
38. Shtukenberg, A. G. Punin, Y. O. Gunn, E. & Kahr, B. Spherulites, *Chem. Rev.* 112, 1805-1838 (2012).
39. Shtukenberg, A. G. Zhu, X. Yang, Y. Kahr, B. Common occurrence of twisted molecular crystal morphologies from the melt. *Cryst. Growth Des.* 20, 6186-6197 (2020).
40. Mitchell, C. A. Yu, L. & Ward, M. D. Selective nucleation and discovery of organic polymorphs through epitaxy with single crystal substrates. *J. Am. Chem. Soc.* 123, 10830-10839 (2001).
41. Yu, L. Nucleation of one polymorph by another. *J. Am. Chem. Soc.* 125, 6380-6381 (2003).
42. Jiang, Q. Ward, M. D. Crystallization under nanoscale confinement. *Chem. Soc. Rev.* 43, 2066-2079 (2014).
43. Schneider, D. Using *Drosophila* as a model Insect. *Nat. Rev. Genet.* 1, 218-226 (2000).
44. Lozano-Fuentes, S. Saavedra-Rodriguez, K. Black, W. C. & Eisen, L. QCal: A software application for the calculation of dose-response curves in insecticide resistance bioassays. *J. Am. Mosq. Control. Assoc.* 28, 59-61 (2012).
45. Grubaugh, N. D. et al. Genomic epidemiology reveals multiple introductions of Zika virus into the United States. *Nature* 546, 401-405 (2017).
46. Metsky, H. C. et al. Zika virus evolution and spread in the Americas. *Nature* 546, 411-415 (2017).
47. Barrett, A. $^D$. T. The reemergence of yellow fever. *Science* 361, 847-848 (2018).
48. Smol, J. P. Climate change: a planet in flux. *Nature* 483, S12-S15 (2012).
49. Riaz, M. A. et al. Molecular mechanisms associated with increased tolerance to the neonicotinoid insecticide imidacloprid in the dengue vector *Aedes aegypti*. *Aquat. Toxicol.* 126, 326-337 (2013).
50. Frisch, G. et al. Gaussian 16, Revision A. 03. (Gaussian, Inc., Wallingford, 2016).
51. Stephens, P. J. Devlin, F. J. Chabalowski, C. F. & Frisch, M. J. Ab initio calculation of vibrational absorption and circular dichroism spectra using density functional force fields. 98, 11623-11627 (1994).
52. Dhananjay, D. Chetan, S. S. Kaushik, B. Deepak, C. CCDC 943833: Experimental Crystal Structure Determination, DOI: 10.5517/cc10p472 (2015).

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A crystalline form of imidacloprid, which is Form IX having a Raman spectrum as shown in FIG. 2.

Figure 12:
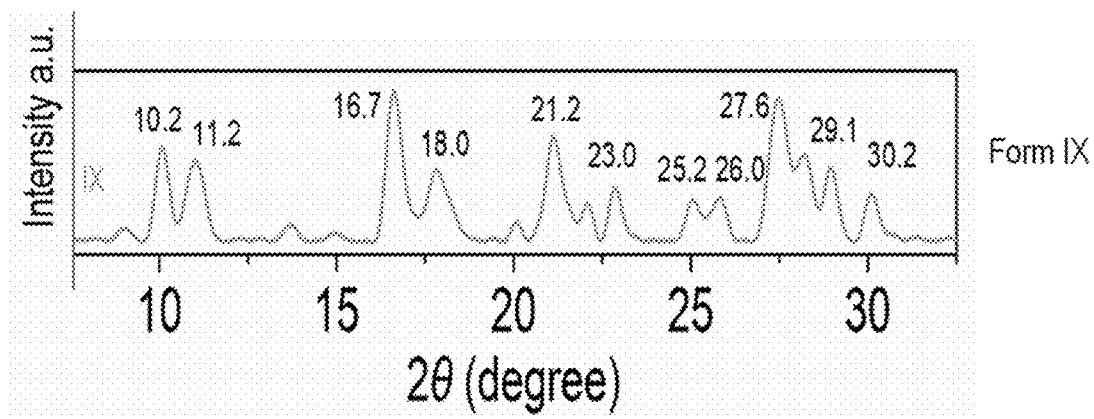
FIG. 12 shows a powder XRD spectrum of imidacloprid Form IX with labeled prominent peaks.
Figure 13:
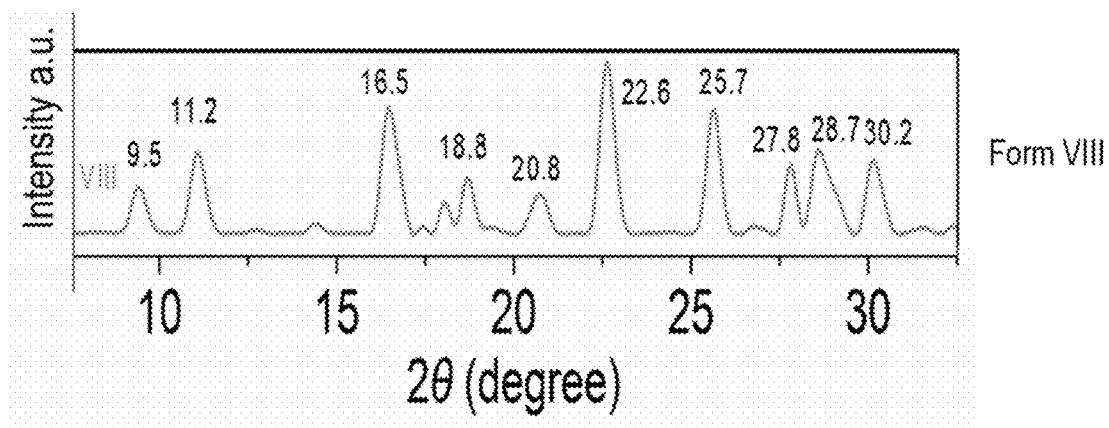
FIG. 13 shows a powder XRD spectrum of imidacloprid Form VIII with labeled prominent peaks.
Figure 14:
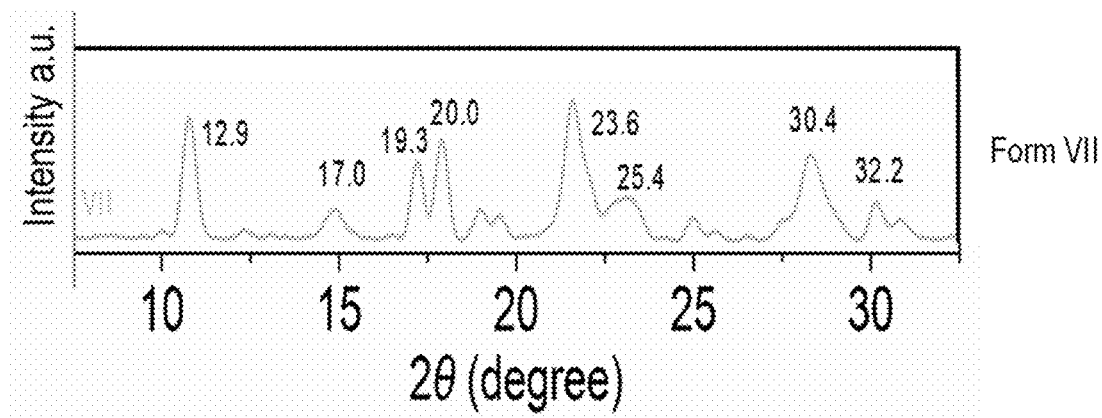
FIG. 14 shows a powder XRD spectrum of imidacloprid Form VII with labeled prominent peaks.
Figure 15:
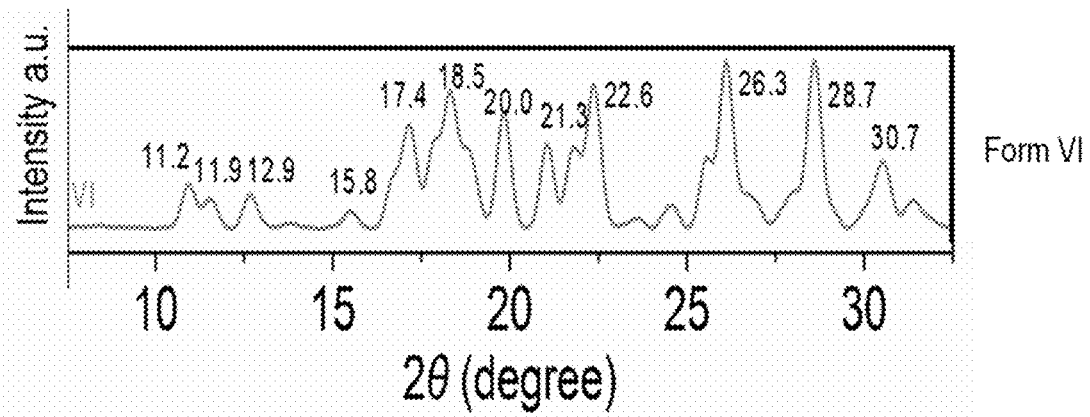
FIG. 15 shows a powder XRD spectrum of imidacloprid Form VI with labeled prominent peaks.
Figure 16:
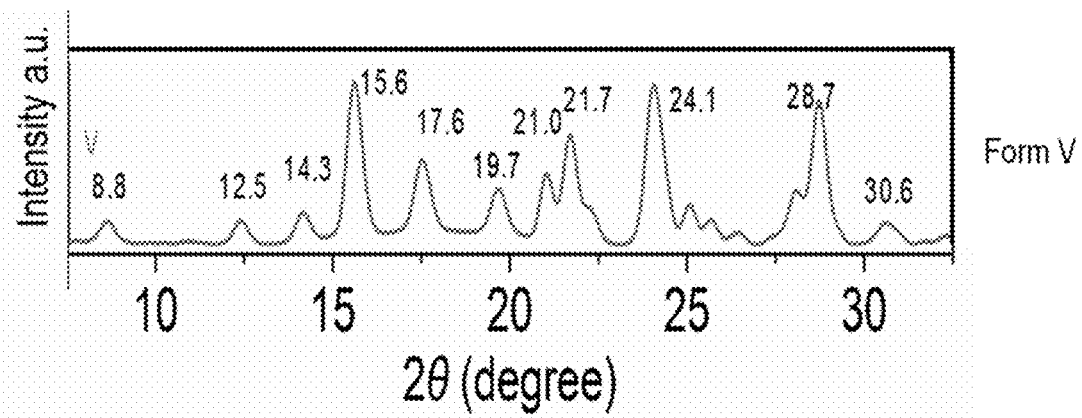
FIG. 16 shows a powder XRD spectrum of imidacloprid Form V with labeled prominent peaks.
Figure 17:
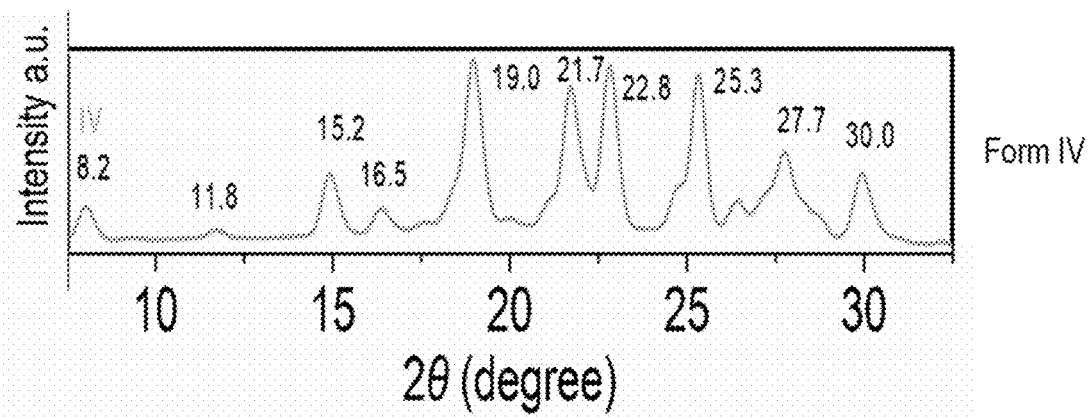
FIG. 17 shows a powder XRD spectrum of imidacloprid Form IV with labeled prominent peaks.
Figure 18:
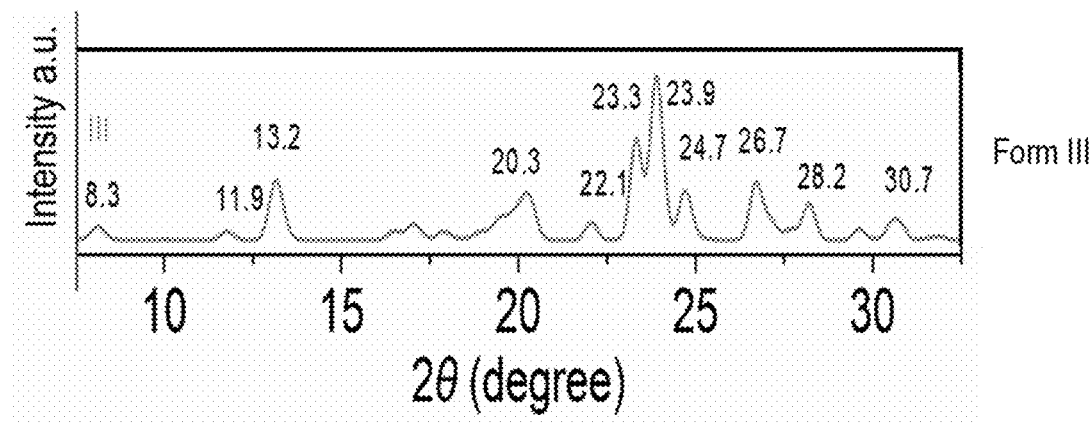
FIG. 18 shows a powder XRD spectrum of imidacloprid Form III with labeled prominent peaks.
Figure 19:
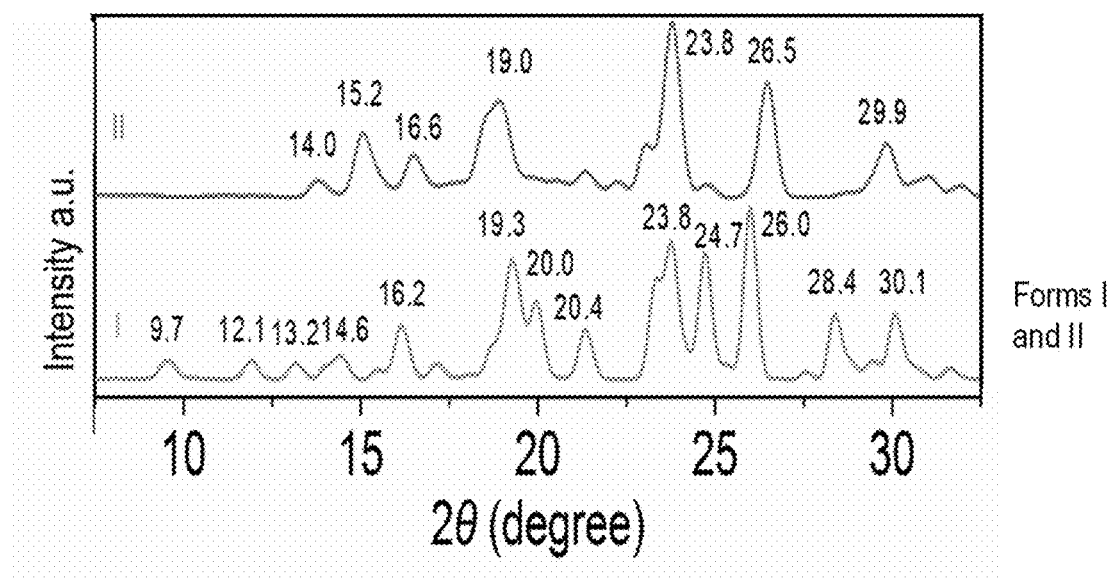
FIG. 19 shows powder XRD spectra of imidacloprid Forms I and II with labeled prominent peaks.

2. The crystalline form of claim 1, which is Form IX having an X-ray diffraction pattern substantially as shown in FIG. 12.

3. The crystalline form of claim 1, which is Form IX having an X-ray diffraction pattern comprising peaks at 10.2, 11.2, 16.7, 18.0, 21.2, 23.0, 25.2, 26.0, 27.6, 29.1, and 30.2 degrees two-theta (2θ).

4. A process for preparing the crystalline Form IX of claim 1, comprising:
   melting imidacloprid Form I at 180° C.; and
   cooling the molten imidacloprid to ambient temperature.

5. The crystalline form of claim 1, wherein the crystalline form is substantially isolated.

6. The crystalline form of claim 1, wherein the crystalline form is substantially free of other crystalline forms.

7. A pesticidal composition comprising the crystalline form of claim 1.

8. The pesticidal composition of claim 7, wherein the crystalline form is present in the composition in an amount of about 0.5% to about 75% by weight.

9. A method of controlling a pest comprising applying to the pest or its locus the crystalline form of claim 1, wherein the pest is an insect selected from *Drosophila, Aedes, Anopheles*, and *Culex*.

10. The method of claim 9, wherein the pest is a disease vector.

11. The method of claim 10, wherein the disease is selected from Zika virus, yellow fever, dengue fever, chikungunya virus, filariasis, West Nile fever, Japanese encephalitis, Rift Valley fever, and combinations thereof.

12. A method of controlling a pest comprising applying to the pest or its locus the pesticidal composition of claim 7, wherein the pest is an insect selected from *Drosophila, Aedes, Anopheles*, and *Culex*.

13. The method of claim 12, wherein the pest is a disease vector.

14. The method of claim 13, wherein the disease is selected from Zika virus, yellow fever, dengue fever, chikungunya virus, filariasis, West Nile fever, Japanese encephalitis, Rift Valley fever, and combinations thereof.

* * * * *